(12) United States Patent
Kim et al.

(10) Patent No.: US 12,102,952 B2
(45) Date of Patent: Oct. 1, 2024

(54) PORTABLE AIR PURIFIER

(71) Applicant: LG ELECTRONICS INC., Seoul (KR)

(72) Inventors: Gyeongho Kim, Seoul (KR); Sangjin Park, Seoul (KR); Jae Woo Kim, Seoul (KR); Dooyeong Kwak, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 381 days.

(21) Appl. No.: 17/542,703

(22) Filed: Dec. 6, 2021

(65) Prior Publication Data

US 2022/0184542 A1      Jun. 16, 2022

(30) Foreign Application Priority Data

Dec. 14, 2020   (KR) .................. 10-2020-0174529
Dec. 30, 2020   (KR) .................. 10-2020-0188336

(51) Int. Cl.
*B01D 46/00*      (2022.01)
*A61L 9/20*       (2006.01)
*B01D 46/66*      (2022.01)

(52) U.S. Cl.
CPC ............ *B01D 46/0049* (2013.01); *A61L 9/20* (2013.01); *B01D 46/0002* (2013.01); *B01D 46/0028* (2013.01); *B01D 46/66* (2022.01); *A61L 2209/12* (2013.01); *A61L 2209/15* (2013.01); *B01D 2273/30* (2013.01); *B01D 2279/65* (2013.01)

(58) Field of Classification Search
CPC ........................... B01D 46/00; B01D 46/0002
See application file for complete search history.

(56) References Cited

U.S. PATENT DOCUMENTS

| 9,943,794 | B2 * | 4/2018 | Jung .................. F24F 8/108 |
| 11,339,985 | B2 * | 5/2022 | Shimizu ................ F24F 8/10 |
| 2020/0061231 | A1 | 2/2020 | Jeong et al. |

FOREIGN PATENT DOCUMENTS

| EP | 2184554 | 5/2010 |
| EP | 3211337 | 8/2017 |
| KR | 10-2014-0039703 | 4/2014 |
| KR | 10-2015-0009361 | 1/2015 |

OTHER PUBLICATIONS

European Search Report dated May 10, 2022 issued in Application No. 21212474.7.

* cited by examiner

*Primary Examiner* — Robert A Hopkins
(74) *Attorney, Agent, or Firm* — KED & ASSOCIATES

(57) ABSTRACT

A portable air purifier is provided that may include a fan module disposed between a suction opening and a discharge opening, a filter disposed between the suction opening and the fan module, and a lighting portion disposed between the discharge opening and the fan module.

17 Claims, 11 Drawing Sheets

PORTABLE AIR PURIFIER

CROSS-REFERENCE TO RELATED APPLICATION(S)

This application claims priority to and the benefit of Korean Patent Application No. 10-2020-0174529, filed in Korea on Dec. 14, 2020 and Korean Patent Application No. 10-2020-0188336, filed in Korea on Dec. 30, 2020, the disclosure of which is incorporated herein by reference in its entirety.

BACKGROUND

1. Field

A portable air purifier is disclosed herein.

2. Background

Air purifiers are devices that are widely used in our daily lives. The devices can filter physical particles, such as dust, fine dust, and ultra-fine dust, for example, chemical substances, such as odorant particles, and harmful gases, for example, and microorganisms, such as germs, and viruses, for example, to purify air. People cannot live without air purifiers in an industrial society, as more and more people are greatly affected by fine dust and suffer from allergies. Accordingly, there is a growing demand for these devices.

Ordinarily, a large-sized air purifier is used in a house that is 100 square meters or greater. The air purifier may be provided with a filter for physical particles, such as dust, for example, a filter for chemical substances, such as gas, for example, and a filter for microorganisms, such as germs, and viruses, for example. That is, such a large-sized air purifier capable of accommodating various types of filters may be used in a large space.

However, air purifiers are rarely used in a narrow or small space, such as a studio apartment, or a space in a vehicle, for example, or in a very wide or large space, such as a public library, for example, or an outdoor space, considering space availability, mobility, and energy efficiency. Additionally, a user who moves from place to place usually uses an air purifier small enough to carry. Under these circumstances, there is a growing need for a portable air purifier that is easy to carry for use.

Portable air purifiers need to be small and lightweight enough for users to carry such that the users may easily carry and use the portable air purifiers anywhere. That is, the portable air purifiers are useful for people who often go out and move from place to place instead of staying in a place, such as a house.

An air purifier is disclosed in U.S. Patent No. 2020/0061231 (hereinafter "related art document"), which is hereby incorporated by reference. The air purifier of the related art document suctions air through a lower side of a front surface thereof, and the suctioned air moves upward through a body. The air moving upward through an inside of the body passes through a plurality of filters and fans consecutively, and then is discharged from an upper side of the body through a discharge opening.

According to related art document, a suction opening is formed on one lateral surface of a lower portion of the body. When the air purifier is held in a structure, such as a cup holder in the form of a groove which is concave downward, the suction opening is disposed in the structure, causing difficulty in suctioning of air through the suction opening.

As a portable air purifier is small and lightweight to be carried easily, an air discharge range of the portable air purifier is narrower than that of a large-sized air purifier. To improve air purification performance of the portable air purifier, it would be better to direct discharge of air purified by the portable air purifier toward a user's face.

However, the air purifier according to the related art document discharges purified air only through the upper side of the body, and is provided with no means of adjusting a discharge direction of the air. Accordingly, when the air purifier is held in a structure, such as the cup holder, discharge of air purified in the air purifier is not directed toward a user's face. Additionally, as the portable air purifier is easily carried and used in different places, the portable air purifier is likely to provide various functions in addition to the function of purifying air.

BRIEF DESCRIPTION OF THE DRAWINGS

Embodiments will be described in detail with reference to the following drawings in which like reference numerals refer to like elements, and wherein.

DETAILED DESCRIPTION

Figure 1:
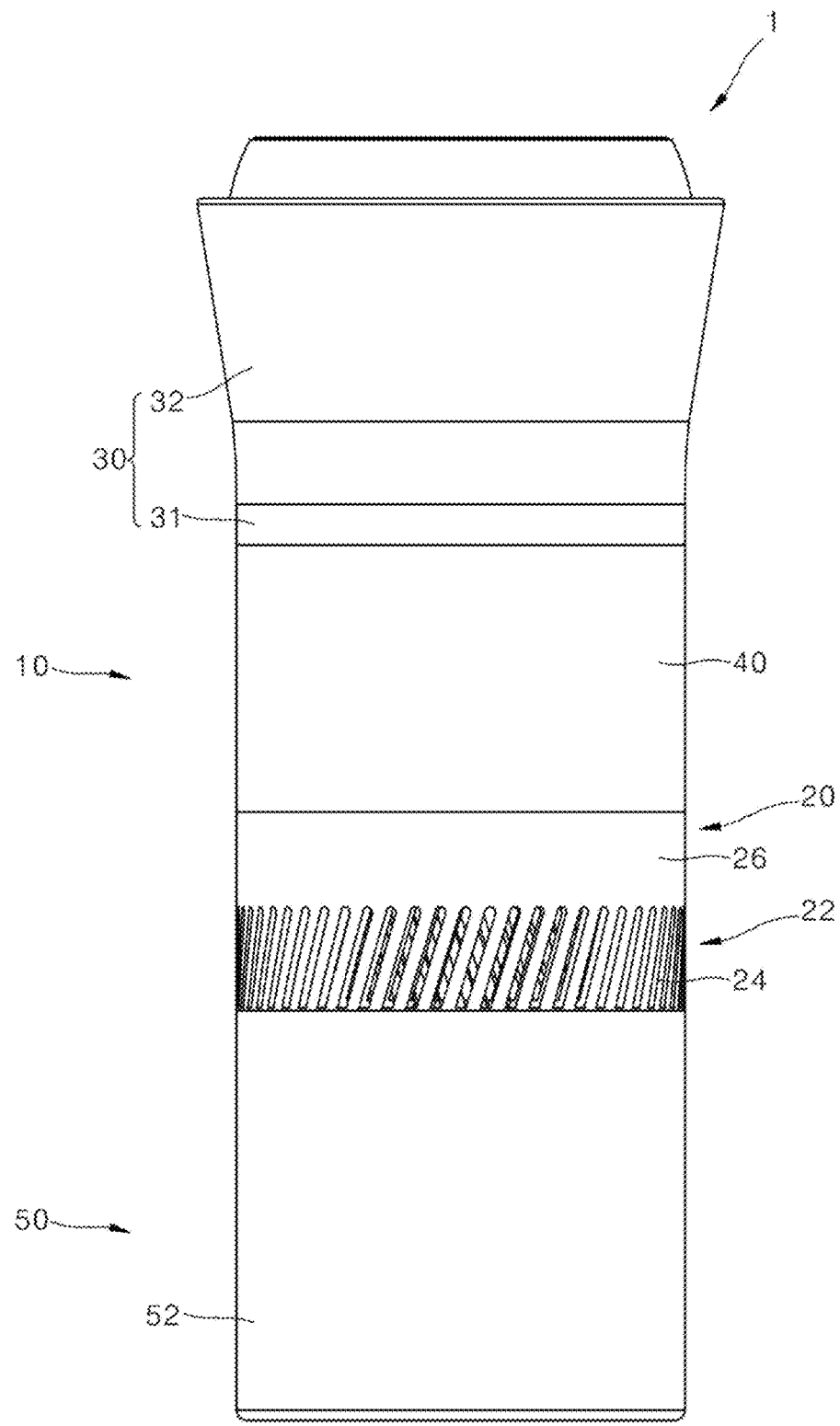
FIG. 1 is a front view showing an exterior of a portable air purifier according to an embodiment.

Features and advantages are described hereinafter with reference to the accompanying drawings such that one having ordinary skill in the art to which embodiments pertain may easily implement the technical spirit. In the disclosure, detailed descriptions of known technologies in relation to the disclosure are omitted if they are deemed to make the gist of the disclosure unnecessarily vague. Hereinafter, embodiments are specifically described with reference to the accompanying drawings. In the drawings, identical reference numerals denote identical or similar components.

The terms "first", and "second", for example are used herein only to distinguish one component from another component. Thus, the components should not be limited by the terms. Certainly, a first component can be a second component unless stated to the contrary.

Embodiments are not limited to the embodiments set forth herein, and may be modified and changed in various different forms. The embodiments are provided such that the disclosure may be thorough and complete and the scope fully conveyed to one of ordinary skill in the art. Accordingly, all modifications, equivalents, or replacements as well as a replacement of the configuration of one embodiment with the configuration of another embodiment or an addition of the configuration of one embodiment to the configuration of another embodiment, within the technical spirit and scope, should be construed as being included in the scope.

Accompanying drawings are provided for a better understanding of the embodiments set forth herein and are not intended to limit the technical spirit. It is to be understood that all the modifications, equivalents, or replacements within the spirit and technical scope are included in the scope of the disclosure. Sizes or thicknesses of components in the drawings are exaggerated or reduced to ensure ease of understanding. However, the protection scope of the subject matter should not be interpreted in a limited way.

The terms in the disclosure are used only to describe specific implementations or embodiments but not intended to limit the subject matter. The singular forms "a", "an" and "the" are intended to include the plural forms as well, unless explicitly indicated otherwise. It is to be understood that the terms "comprise", and "include", for example, set forth herein, are used to indicate presence of features, numbers, steps, operations, components, parts or combinations thereof, and do not imply the exclusion of one or more additional features, numbers, steps, operations, components, parts or combinations thereof.

The terms "first", "second", for example are used herein only to distinguish one component from another component. Thus, the components should not be limited by the terms. Certainly, a first component can be a second component unless stated to the contrary.

When one component is described as being "connected" or "connected" to another component, one component can be directly connected or connected to another component. However, it is also to be understood that an additional component can be "interposed" between the two components. When one component is described as being "directly connected" or "directly connected" to another component, it is to be understood that no additional component is interposed between the two components.

When one component is described as being "on" or "under" another component, one component can be directly on or under another component, and an additional component can be interposed between the two components.

Unless otherwise defined, all the terms (technical or science words) used herein have the same meaning as commonly understood by one of ordinary skill in the art. Additionally, terms such as those defined in commonly-used dictionaries should be interpreted as having a meaning that is consistent with their meaning in the context of the relevant art, and unless explicitly defined herein, should not be interpreted in an ideal or overly sense.

In a state in which a portable air purifier stands on the floor, with respect to a center of the portable air purifier, a direction toward the floor is defined as a downward direction and a direction toward a discharge is defined as an upward direction. For convenience, a direction facing the downward direction and the upward direction can be referred to as a first direction. Then the downward direction is referred to as one direction of the first direction, and the upward direction is referred to as the other direction of the first direction.

Additionally, a gravitational direction may be defined as the downward direction, and a direction opposite to the gravitational direction may be defined as the upward direction.

Further, a horizontal direction across a vertical direction of the portable air purifier, that is, a widthwise direction of the portable air purifier as viewed from a front of the portable air purifier in a state of standing on the floor may be referred to as a leftward-rightward direction.

For convenience, the leftward-rightward direction may be referred to as a second direction. Then the right side may be referred to as one direction of the second direction, and a left side may be referred to as the other direction of the second direction.

Additionally, the widthwise direction of the portable air purifier may also be referred to as a lateral direction. The right side may also be referred to as one side of the lateral direction, and the left side may be referred to the other side of the lateral direction.

Further, a horizontal direction across the first direction and the second direction of the portable air purifier may be referred to as a frontward-rearward direction of the portable air purifier. For convenience, the frontward-rearward direction may be referred to as the first direction, and a front may be referred to as one direction of a third direction while a rear may be referred to as the other direction of the third direction.

Furthermore, a direction, in which a flat surface parallel with the second direction and the third direction of the portable air purifier extends, may be referred to as a flat surface direction for convenience.

Hereinafter, the terms "A and/or B" as used herein can denote A, B or A and B, and the terms "C to D" can denote C or greater and D or less, unless stated to the contrary.

Figure 2:
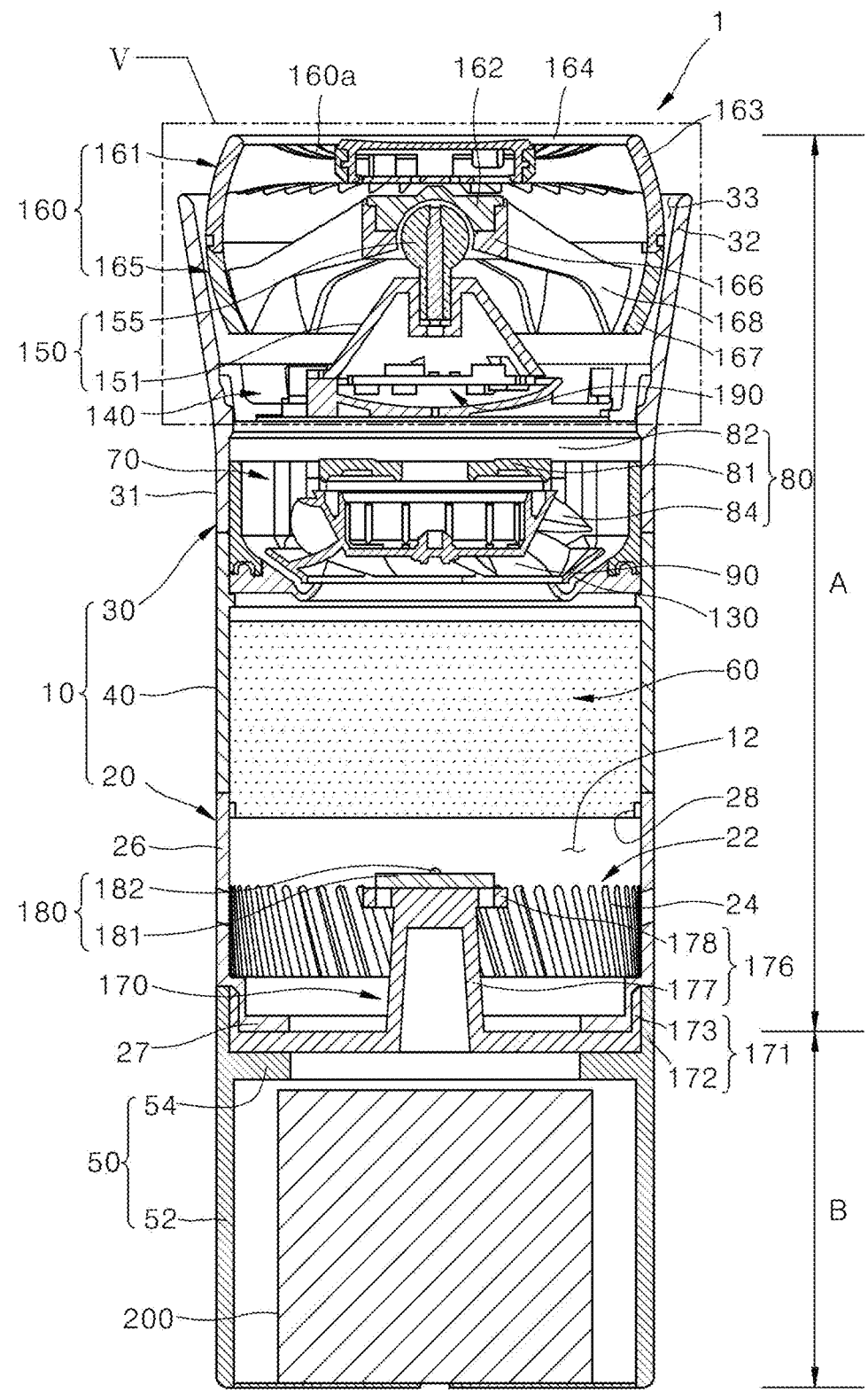
FIG. 2 is a cross-sectional view showing an inner structure of the portable air purifier of FIG. 1.

FIG. 1 is a front view showing an exterior of a portable air purifier according to an embodiment. FIG. 2 is a cross-sectional view showing an inner structure of the portable air purifier of FIG. 1.

Referring to FIGS. 1 and 2, portable air purifier 1 according to an embodiment may be formed into an approximate cylinder. The portable air purifier 1 may include at least one of a housing 10, 50, a discharge outlet 160, and a filter 60.

The housing 10, 50 may be provided with an inlet 22, and the filter 60 and a fan module 70 may be disposed inside the housing 10, 50. Additionally, the housing 10, 50 may form an air path in a vertical direction. That is, inside of the housing 10, 50, a cylindrical air path may be formed. Accordingly, frictional resistance against air moving inside of the housing 10, 50 in the vertical direction may decrease.

Additionally, centers of the inlet 22, the filter 60, the fan module 70, and a first discharge opening 33 may be aligned in the vertical direction along a perpendicular reference line that passes through a center of the housing 10, 50 in the vertical direction. Accordingly, a flow of air moving in the housing 10, 50 may be formed into a straight line along a perpendicular direction. Thus, a length of the flow of the air and flow resistance of the air, in the housing 10, 50, may decrease, thereby contributing to improvement in air purification efficiency of the portable air purifier 1. When the portable air purifier 1 is placed on a horizontal surface, the perpendicular reference line may be aligned with a perpendicular line.

Further, the housing 10, 50 may include first housing 10 and second housing 50. In this embodiment, air may be suctioned into the housing 10, 50 through a lateral surface of the first housing 10, and the air suctioned into the housing 10, 50 may be discharged from an upper portion of the housing 10, 50, for example.

The first housing 10 and the second housing 50 may form a skeleton of an exterior of the portable air purifier 1. A plurality of components may be accommodated in the first housing 10 and the second housing 50.

The first housing 10 may be formed into an approximate cylinder, for example. The first housing 10 may have an accommodating space therein. The filter 60 and the fan module 70 may be disposed in the accommodating space of the first housing 10.

The first housing 10 may be formed in a way such that both first direction sides of the first housing 10 are open. That is, upper and lower sides of the first housing 10 may be open. The inlet 22 may be disposed at one first-direction side of the first housing 10, and the first discharge opening 33 and the discharge outlet 160 may be disposed at the other first-direction side of the first housing 10.

The second housing 50 may connect to a lower side of the first housing 10. Like the first housing 10, the second housing 50 may be formed into a cylinder.

The portable air purifier 1 may be entirely formed into a cylinder having a length of a lateral surface greater than a diameter of a bottom surface. A user may use the portable air purifier 1 in a state in which the portable air purifier 1 stands or lies down. Additionally, as the portable air purifier 1 may be used in a state of being held in a groove which is concave downward, such as a cup holder, in a location, for example, inside of a vehicle which is being driven, the portable air purifier 1 may stay in the same position reliably.

Directions are defined as follows. Under the assumption that a portion from the first housing 10 to the discharge outlet 160 is referred to as an upward direction and that a portion from the first housing 10 to the second housing 50 is referred to as a downward direction, a "first direction" indicates a vertical direction or an axial direction. Additionally, the "first direction" may denote the same direction as the perpendicular direction. Further, a "second direction" denotes a direction perpendicular to the first direction and a lateral direction or radial direction.

The portable air purifier 1 may include the first housing 10, the second housing 50, the filter 60, the fan module 70, and the discharge outlet 160. As set forth above, the first housing 10 and the second housing 50 may form a skeleton of the exterior of the portable air purifier 1. Exteriors of a lateral surface and a bottom surface of the portable air purifier 1 may be formed by the first housing 10 and the second housing 50.

The first housing 10 and the second housing 50 may have an accommodating space 12 therein. Electronic components including the filter 60, the fan module 70, a sterilizer 170, and a battery 200, for example, may be accommodated in the accommodating space 12. The first housing 10 and the second housing 50 may be strong enough to protect the accommodated components from an external impact, for example.

The filter 60 may be disposed in the accommodating space 12 of the first housing 10. More specifically, the filter 60 may be disposed between the fan module 70 and the inlet 22. The filter 60 may be disposed under the fan module 70, and purify air suctioned through the inlet 22 of the portable air purifier 1. The air, which is purified while passing through the filter 60, may pass through the fan module 70 and the discharge outlet 160 and then be discharged from an upper portion of the portable air purifier 1.

The filter 60 may be disposed inside of the first housing 10, and purify air suctioned into the inlet 22. For example, the filter 60 may be in the form of a cylinder corresponding to a shape of the first housing 10. The filter 60 may be a single filter, or when necessary, a plurality of filters in a state of being stacked.

Additionally, the portable air purifier 1 may be further provided with a filter case that fixes the filter 60. For example, the filter case may be fixed to an inside of the first housing 10, and have an insertion space that accommodates the filter 60, therein.

The fan module 70 may be accommodated in the accommodating space 12 of the first housing 10 and disposed between the discharge outlet 160 and the filter 60. More specifically, the fan module 70 may be disposed between the first discharge opening 33 and the filter 60.

That is, the fan module 70 may be disposed over the filter 60, and the first discharge opening 33 and the discharge outlet 160 may be disposed over the fan module 70. The fan module 70 may suction external air through the inlet 22, and discharge the air from the upper portion of the first housing 10.

A rotational center of the discharge outlet 160 may be aligned with a center of the fan module 70 in the vertical direction. Air suctioned through the inlet 22 may pass through the filter 60 and the fan module 70 consecutively while moving upward, and then be discharged from the upper portion of the portable air purifier 1 through the discharge outlet 160.

In this embodiment, the fan module 70 includes a mixed flow fan, for example. The fan module 70 may suction the air having passed through the filter 60 in the axial direction and then discharge the air in a direction between the axial direction and the radial direction.

The discharge outlet 160 may be rotatably disposed over the first housing 10 and guide a discharge direction of air which is moved upward through the first discharge opening 33. Support modules 140, 150 may be disposed between the discharge outlet 160 and the fan module 70, and the discharge outlet 160 may be supported by the support modules 140, 150.

The discharge outlet 160 may be provided with a second discharge opening 160a. The second discharge opening 160a may penetrate the discharge outlet 160 in the vertical direction. The second discharge opening 160a may form a passage that connects an upper portion of the discharge outlet 160 and the first discharge opening 33. Air moved to the upper portion of the first housing 10 through the first discharge opening 33 may be discharged out of the portable air purifier 1 through the second discharge opening 160a of the discharge outlet 160.

The discharge outlet 160 may be rotatably mounted onto the support modules 140, 150. As the discharge outlet 160 is rotatably mounted onto the support modules 140, 150, an orientation of the discharge outlet 160 may change. Based on a change in the orientation of the discharge outlet 160, a position and a direction of the second discharge opening 160a may change. Accordingly, the discharge direction of air may be adjusted, using the discharge outlet 160.

The portable air purifier 1 may further include a sterilizer 170. The sterilizer 170 may be disposed below the filter 60 and fixed to at least one of the first housing 10 or the second housing 50. The sterilizer 170 may be spaced a predetermined distance apart from the filter 60, and in the state of being spaced from the filter 60, irradiate light rays for sterilization toward the filter 60.

When the light rays for sterilization irradiated from the sterilizer 170 are harmful to the human body, a position of the sterilizer 170 needs to be adjusted to prevent the light rays from leaking out of the portable air purifier 1 through the inlet 22.

The battery 200 may be disposed in the accommodating space 12 provided inside of the second housing 50. For example, the battery 200 may be disposed under the sterilizer 170. The battery 200 may supply power to the portable air purifier 1, to drive the portable air purifier 1.

The accommodating space 12 provided in the portable air purifier 1 may be divided into a first area A and a second area B. When the accommodating space 12 is divided in the vertical direction, an upper area becomes the first area A, and a lower area under the upper area becomes the second area B. The first area A and the second area B are not areas which are divided physically but areas which are divided conceptually. For example, the accommodating space 12 of the first housing 10 forming the skeleton of the portable air purifier 1 may be set as the first area A, and the accommodating space 12 in the second housing 50 forming the skeleton of the portable air purifier 1 may be set as the second area B.

Components in relation to suction, purification, and discharge of air may be disposed in the first area A. That is, the inlet 22, the filter 60, the fan module 70 and the discharge outlet 160 may be disposed in the first area A. In the first area A, air may flow from a lower side to an upper side.

The first housing 10 may be provided with the inlet 22 as a passage through which air is suctioned. The inlet 22 may include a plurality of suction openings 24. Each of the suction openings 24 may be formed in such a way that penetrates a lateral portion of the first housing 10 in the radial direction.

The first discharge opening 33 may be disposed on the first housing 10, and the discharge outlet 160 may be disposed on the first discharge opening 33. The discharge outlet 160 may be provided in the first area A as a passage through which purified air is discharged. The discharge outlet 160 may include a plurality of second discharge openings 160a, and air purified in the first area A may be discharged out of the portable air purifier 1 through the second discharge opening 160a.

Additionally, an air path that connects the filter 60, the fan module 70, and the discharge outlet 160 may be formed in the first housing 10. That is, the inlet 22, the filter 60, the fan module 60, and the discharge outlet 160 may be provided in the first area A, and a path through which air is suctioned into the portable air purifier 1 pass through the air purifier 1 may be formed in the first area A.

Components, which do not directly relate to a flow of air for air purification, may be disposed in the second area B. For example, a controller including a printed circuit board (PCB), and the battery 200, for example, may be installed in the second area B.

The first housing 10 and the second housing 50 may be formed into a cylinder having a vertical direction length greater than a lateral direction length. The first area A disposed in the upper portion may have a vertical direction length greater than a vertical direction length of the second area B disposed in the lower portion. That is, when the portable air purifier 1 stands in the vertical direction, the first area A in the upper portion takes up a larger area than the second area B in the lower portion.

The battery 200 may be installed inside of the second housing 50 including the second area B. The battery 200 may have weight greater than a total of a weight of the fan module 70, a weight of the filter 60, and a weight of the discharge outlet 160. As weight per unit volume of the battery 200 is ordinarily much greater than weight per unit volume of the fan module 70, the filter 60, and the discharge outlet 160, the battery 200 weighs more than the fan module 70, the filter 60, and the discharge outlet 160 even without intentionally increasing the weight or the size of the battery 200.

When the battery 200 which is a heavy object is disposed in a lower portion of the portable air purifier 1, a center of gravity of the portable air purifier 1 may be displaced from a center in the vertical direction to a lower portion. That is, the center of gravity of the portable air purifier 1 moves to the lower portion of the portable air purifier 1, in which the battery 200 is disposed.

When the center of gravity of the portable air purifier 1 is eccentric to a lower side of the portable air purifier 1, at which the battery 200 is disposed, the portable air purifier 1 is unlikely to fall when the portable air purifier 1 stands. That is, when the portable air purifier 1 stands in the vertical direction, the portable air purifier 1 is unlikely to fall as the center of gravity of the portable air purifier 1 is located at the lower side of the portable air purifier 1 thanks to the battery 200 being disposed in the lower portion of the portable air purifier 1.

When the battery 200 which is a heavy object is disposed in the lower portion of the portable air purifier 1, other components of the portable air purifier 1 need to be disposed further upward than the battery 200. That is, the components in relation to suction, purification, and discharge of air need to be disposed higher than the battery 200.

To ensure that a charge capacity of the battery 200 needed to operate the portable air purifier 1 is sufficient, the battery 200 needs to have a predetermined size or greater. Accordingly, the portable air purifier 1 needs to have a space therein, which has a predetermined size or greater in which to install the battery 200. Further, as a path for air flow may hardly be formed in the space in which the battery 200 is installed, components in relation to suction, purification, and discharge of air need to be disposed in a position except for the position of the battery 200, that is, in a position higher than the position of the battery 200.

In the portable air purifier 1 having such structure, a path for suction, purification, and discharge of air may be formed in the first area A which is higher than the position of the battery 200. Accordingly, suction of air into the portable air purifier 1 and discharge of air purified by the portable air purifier 1 may be performed in a position higher than the position of the battery 200.

When the purified air is discharged from the upper portion of the portable air purifier 1, as described above, the air purified in the portable air purifier 1 may reach the user's face more easily. When the portable air purifier 1 is placed and used on the floor which is a position lower than the position of the user's face, a larger amount of the air purified in the portable air purifier 1 may reach the user's face, in a state in which the portable air purifier 1 stands rather than lies down.

Thus, the portable air purifier 1 may stand vertically, and the purifier air may be discharged from the upper portion of the portable air purifier 1. Then a larger amount of the air purified in the portable air purifier 1 may reach the user's face.

Additionally, with the structure in which the battery 200 is disposed in the lower portion of the portable air purifier 1, and the components in relation to suction, purification, and discharge of air are disposed in a position higher than the position of the battery 200, the portable air purifier 1 may be installed in a wide range of places. For example, when the portable air purifier 1 is used in a state of being held in a cup holder of a vehicle, an area in which air is suctioned, and an area in which air is purified and discharged may be at a position higher than the position of the cup holder. Accordingly, the portable air purifier 1 may ensure high-level air purification performance while being placed reliably in the vehicle. Thus, the vertical direction length of the second area B in which the battery 200 is disposed may be set to a depth or greater of the cup holder, for example.

As another example, when a lower area of the portable air purifier 1 is fixed with a tong-type holder, for example, the portable air purifier 1 may be fixed reliably while the portable air purifier's area for suctioning air and area for discharging purified air are not blocked. When the user holds the lower portion of the portable air purifier 1 and moves the portable air purifier 1, the portable air purifier 1 may be carried reliably while the portable air purifier 1's area for suctioning air and area for discharging purified air are not blocked.

That is, components such as the battery 200 which does not directly relate to flow of air for air purification may be disposed in the lower portion of the portable air purifier 1, and the portable air purifier 1 may be held and fixed, using the lower portion thereof, to ensure high-level air purification performance of the portable air purifier 1 and reliable fixation of the portable air purifier 1.

In the portable air purifier 1 according to an embodiment, having the above structure, the first housing 10 provided with the inlet 22 may be disposed at an upper side of the second housing 50. The first housing 10 may connect to the upper side of the second housing 50 in which electronic components are installed, and the first housing 10 may be provided with the inlet 22 through which air is suctioned.

For example, the second housing 50 may have a depth corresponding to a depth of a structure formed into a groove, such as a cup holder which is concave downward, and the inlet 22 may be disposed further upward than the second housing 50. Thus, in a state in which the first housing 10 is inserted into the structure formed into a groove, such as a cup holder which is concave downward, the inlet 22 may be disposed in a position exposed upward from the structure, such as a cup holder.

Air may be effectively suctioned into the first housing 10 through the inlet 22 exposed upward from the structure, such as a cup holder, and air purified in the first housing 10 may be discharged from the upper side of the first housing 10 through the discharge outlet 160. That is, even when the portable air purifier 1 is inserted into the structure, such as a cup holder, air suction and air discharge of the portable air purifier 1 may be smoothly performed. Thus, the portable air purifier 1 may ensure high-level air purification efficiency even when the portable air purifier 1 is inserted into the structure, such as a cup holder.

The first housing 10 may have accommodating space 12 therein. The first housing 10 may be provided with inlet 22, in a lower portion of a lateral surface thereof. The first housing 10 may be formed into a cylinder having both vertical direction sides open. The first housing 10 may be a single component, or when necessary, a plurality of components.

In this embodiment, the first housing 10 is formed in such a way that a plurality of components is coupled, for example. For example, each of the components forming the first housing 10 may be fitted-coupled to one another, or coupled to one another by an adhesive. As another example, each of the components forming the first housing 10 may be coupled to one another by a coupling member, such as a bolt. The coupling of the components forming the first housing 10 may be implemented in various different forms.

As described above, air may be suctioned through the lateral surface of the lower portion of the first housing 10, and discharged through the upper side of the first housing 10. Thus, the first housing 10 may have the inlet 22, on the lateral surface thereof, and have first discharge opening 33, in the upper portion thereof.

The inlet 22 may be formed in such a way that a plurality of suction openings 24 is arranged in a circumferential direction of the first housing 10. The first discharge opening 33 may be formed in the upper portion of the first housing 10 in a way that penetrates in the vertical direction.

The first housing 10 may include at least one of first case 20, second case 30, and middle case 40. In this embodiment, the first housing 10 includes all of the first case 20, the second case 30, and the middle case 40, for example.

The first case 20, the second case 30, and the middle case 40 may be arranged in the vertical direction. For example, the middle case 40 may connect to an upper side of the first case 20, and the second case 30 may connect to an upper side of the middle case 40.

The accommodating space 12 formed inside of the first case 20, the middle case 40, and the second case 30 may communicate in the vertical direction, which is the first direction. Accordingly, air suctioned into the first case 20 may move upward along a passage formed in the middle case 40 and the second case 30.

The first case 20 may be disposed at a lowermost position among positions of the first case 20, the middle case 40, and the second case 30. The first case 20 may be provided with the inlet 22 for suctioning air.

Within the technical scope in which the first case 20 is coupled to the upper side of the second housing 50, the first case 20 may be implemented in various different forms. In this embodiment, the first case 20 is formed into a cylinder, and the second housing 50, the first case 20, and the middle case 40 communicate in the first direction, for example.

The inlet 22 may be installed in a strap-shaped area along a circumference of the first case 20. The inlet 22 may include a plurality of suction openings 24 that guides air into the first housing 10.

Within the technical scope in which the suction opening 24 guides a flow of air suctioned into the first case 20 in a spiral shape, the suction opening 24 may be implemented in various different forms. In this embodiment, the suction opening 24 is formed as a hole that is elongated in the vertical direction, for example. Additionally, the suction opening 24 may be inclined in one direction along an outer circumference of the first housing 10. The suction opening 24 may guide a flow of air suctioned into the first case 1 in a spiral shape.

For example, when a virtual perpendicular line extends in the first direction, each suction opening 24 may be inclined while forming a predetermined angle with respect to a virtual perpendicular line. In this case, each suction opening 24 may be inclined in a direction in which fan 90 disposed in the fan module 70 rotates.

Accordingly, air suctioned into the first case 20 through the suction opening 24 may be suctioned by the fan 90 while rotating in a direction of rotation of the fan 90. That is, the air suctioned into the first case 20 through the suction opening 24 may be suctioned into the fan 90 while rotating spirally along a direction corresponding to the direction of rotation of the fan 90. Thus, a flow of air suctioned into the fan 90 may be created more efficiently, and air suction efficiency of the fan 90 may be improved.

Additionally, as the suction opening 24 is formed into an elongated inclined hole as describe above, an area of an air suction passage formed by the suction opening 24 in this embodiment may be much wider than an area of an air suction passage formed by a suction opening formed into an elongated hole that stands perpendicularly, on the inlet 22. Air suctioned through the inlet 22 may flow more efficiently by as much as the area of the air suction passage formed by the suction opening 24 increases with respect to the same area, thereby improving air purification performance of the portable air purifier 1.

For example, when the fan 90 rotates clockwise, the suction opening 24 may be inclined clockwise. As another example, when the fan 90 rotates counterclockwise, the suction opening 24 may be inclined counterclockwise.

The suction opening 24 may be inclined in an oblique line form as described above, and when necessary, may be formed into an inequality sign-shaped hole with its center bent. As another example, the suction opening 24 may be additionally formed in an area of housing 300, which overlaps the filter 60 in the radial direction. Accordingly, a flow rate of air suctioned into the filter 60 through the inlet 22 may increase. In addition, the suction openings 24 and the inlet 22 formed by the suction opening 24 may be implemented in various different forms.

The filter 60 may be disposed over the inlet 22 in a position in which the filter 60 is spaced upward apart from the inlet 22 by a predetermined distance. Accordingly, a space surrounded by the inlet 22, and a space surrounded by the first housing 10 on the inlet 22 may be formed under the filter 60. Hereafter, a space in which the two spaces are combined is referred to as a "separation space".

Air suctioned into the first housing 10 through the inlet 22 may pass through the separation space before passing through the filter 60. The air suctioned into the separation space may spread across the separation space and then pass through the filter 60 without immediately passing through the filter 60, after the air passes through the inlet 22.

When the air spreads across the separation space and then passes through the filter 60, the air may pass through the filter 60 across the entire area of the filter 60. Accordingly, the air may pass through the filter 60 more efficiently. As the air passes through the filter 60 smoothly, as described above, flow resistance of the air may decrease in an area in which the air passes through the filter 60 after being suctioned through the inlet 22.

Thus, a flow rate of air suctioned into the portable air purifier 1 may increase, and a flow rate of purified air discharged from the portable air purifier 1 may increase by as much as the flow rate of air suctioned into the portable air purifier 1 increases. Thus, air purification performance of the portable air purifier 10 may be further improved.

The first case 20 may include the inlet 22 and shielding body 26. The shielding body 26 may be disposed at an upper side of the inlet 22 that suctions air. The shielding body 26 may be formed into a cylinder. The shielding body 26 may guide the inlet 22 and the filter 60 such that the inlet 22 and the filter 60 are spaced a predetermined distance apart from each other. That is, the separation space may be a space in which a space surrounded by the inlet 22, and at least a portion of a space surrounded by the shielding body 26 are combined.

The first case 20 may further include an upper portion fixing portion 27 that fixes the sterilizer 170. The first case 20 may be disposed on the second housing 50, and a sterilizer support 171 of the sterilizer 170, described hereinafter, may be disposed between the first case 20 and the second housing 50.

The upper portion fixing portion 27 may extend to a lower side of the inlet 22 and be disposed at an upper side of the sterilizer support 171. The upper portion fixing portion 27 may limit an upward movement of the sterilizer 170 including the sterilizer support 171.

In this embodiment, the upper portion fixing portion 27 extends downward at a lower end of the inlet 22 along an inner surface of the first case 20 and then extends in a centripetal direction of the first case 20, for example. The upper portion fixing portion 27 may limit an upward movement of the sterilizer support 171 by pressing an upper portion of the sterilizer support 171 downward.

The first case 20 may further include a filter fixing projection 28 that fixes the filter 60. The filter fixing projection 28 may protrude from an upper portion of the first case 20 to an inside of the first case 20 and support a lower portion of the filter 60. The filter fixing projection 28 may be formed into a projection that protrudes to an inside of the shielding body 26. The filter fixing projection 28 may be inserted into a groove formed in the lower portion of the filter 60 and support the lower portion of the filter 60 to limit downward movement of the filter 60.

The second case 30 may be disposed at the upper side of the first case 20. The second case 30 may have the first discharge opening 33.

Within the technical scope in which the second case 30 rotatably supports the discharge outlet 160, the second case 30 may be implemented in various different forms. A lower portion of the second case 30 may be formed into a cylindrical pipe while an upper portion of the second case 30 may be formed into an expanded pipe, an outlet of which gradually expands. The second case 30 may include at least one of a second case body 31 and a pipe expansion member 32.

The second case body 31 may be formed in such a way that it surrounds an outer circumference of the fan module 70. The second case body 31 may be formed into a cylindrical pipe that extends in the first direction, and the accommodating space 12 formed inside of the second case body 31 may communicate with the middle case 40 and the discharge outlet 160 in the first direction. The fan module 70 may be disposed inside of the second case body 31.

The pipe expansion member 32 may be formed into a pipe that extends to an upper side of the second case body 31 and in which an inner passage gradually expands toward an upper side thereof. A shape of the pipe expansion member 32 may be designed considering a size and a rotational angle of the discharge outlet 160.

The pipe expansion member 32 may be integrated with the second case body 31, and when necessary, the pipe expansion member 32 and the second case body 31 may be separately manufactured and then coupled. The first discharge opening 33 may be formed inside of the pipe expansion member 32, and the discharge outlet 160 may be rotatably disposed on the first discharge opening 33.

The middle case 40 may be disposed between the first case 20 and the second case 30. The middle case 40 may surround an outside of the filter 60.

Within the technical scope in which the first case 20 and the second case 30 connect, the middle case 40 may be implemented in various different forms. In this embodiment, the middle case 40 is formed into a cylindrical pipe, and upper and lower sides of the middle case 40 are open, for example.

The second housing 50 may connect to the lower portion of the first housing 10. Within the technical scope in which a space for installing electronic components including the battery 200 is formed inside of the second housing 50, the second housing 50 may implemented in various different forms.

At least one of the first housing 10 or the second housing 50 may be formed into a cylindrical case. For example, the first housing 10 and the second housing 50 may both be formed into a cylindrical case, and as another example, the second housing 50 may only be formed into a cylindrical case, or when necessary, the first housing 10 may only be formed into a cylindrical case.

When the second housing 50 is formed into a cylinder and extends in the vertical direction, a user may easily take an outer circumference of the second housing 50 in the hand, and the second housing 50 may be reliably held in a cup holder of a vehicle, which is usually provided with a groove having a circular cross section.

When the first housing 10 is formed into a cylinder, air moving in the first housing 10 may move along a curved surface inside of the first housing 10. Accordingly, friction between an inner curved surface of the first housing 10 and the air may decrease, thereby enabling the air to flow more smoothly.

The second housing 50 may include a lower case 52 and a lower portion holder 54. The lower case 52 may be formed into a cylinder, and electronic components including the battery 200 may be installed inside of the lower case 52. An upper side of the lower case 52 may be open, and a lower side of the lower case 52 may be shielded by an additional cover.

The lower portion holder 54 may be disposed at the upper side of the lower case 52, and protrude to an inside of the lower case 52. The lower portion holder 54 may support the sterilizer 170 below the sterilizer 170.

The fan module 70 may be disposed between the filter 60 and the discharge outlet 160. Within the technical scope in which the fan module 70 blows air toward the discharge opening 33 by rotating a fan, the fan module 70 may be implemented in various different forms.

Figure 3:
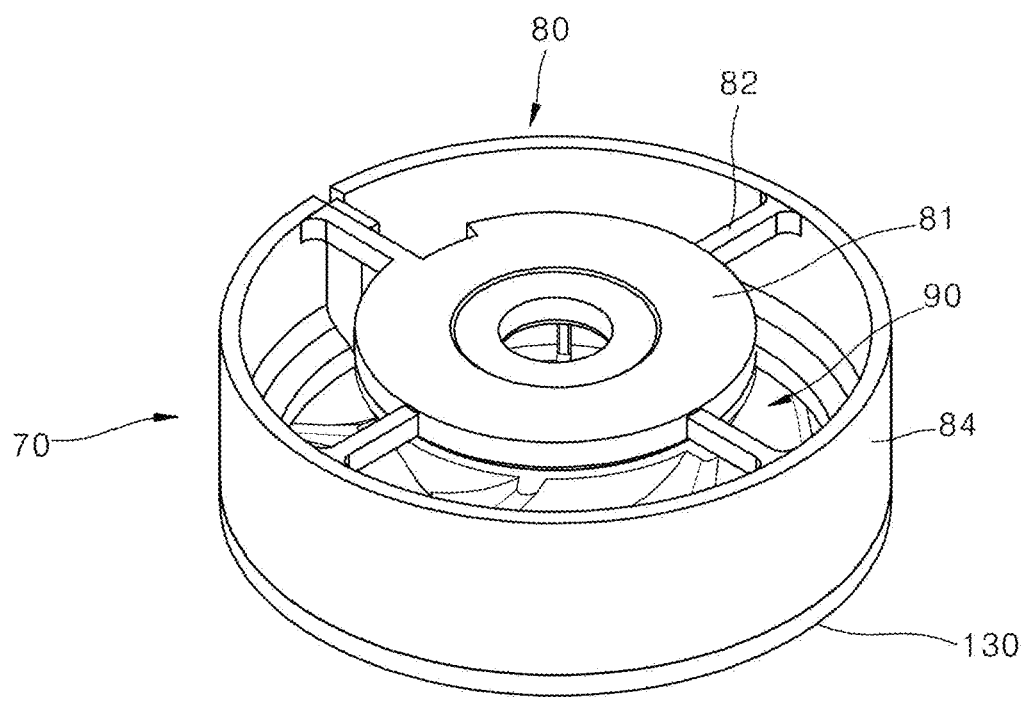
FIG. 3 is a perspective view of a fan module of the portable air purifier of FIG. 2.
Figure 4:
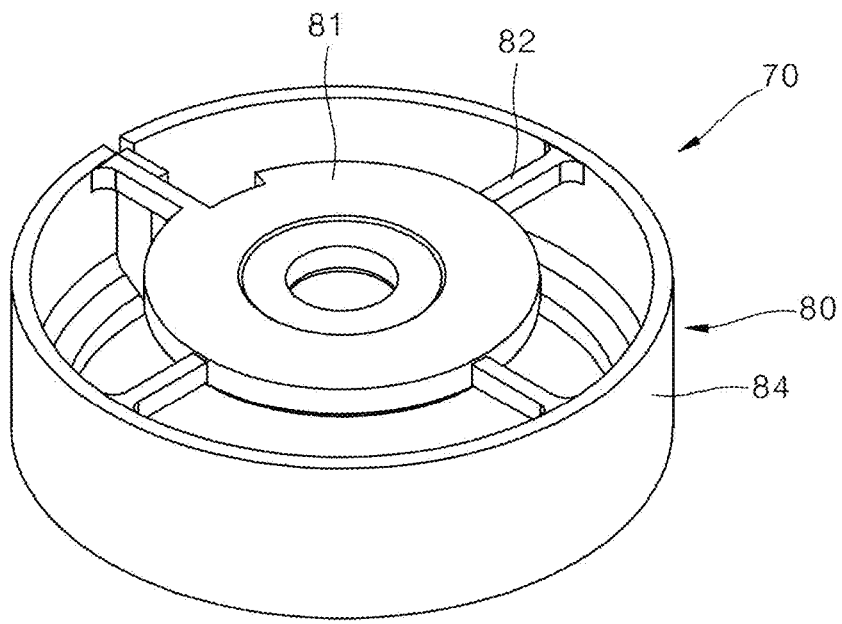
FIG. 4 is an exploded perspective view showing a state in which the fan module in FIG. 3 is disassembled.
Figure 4:
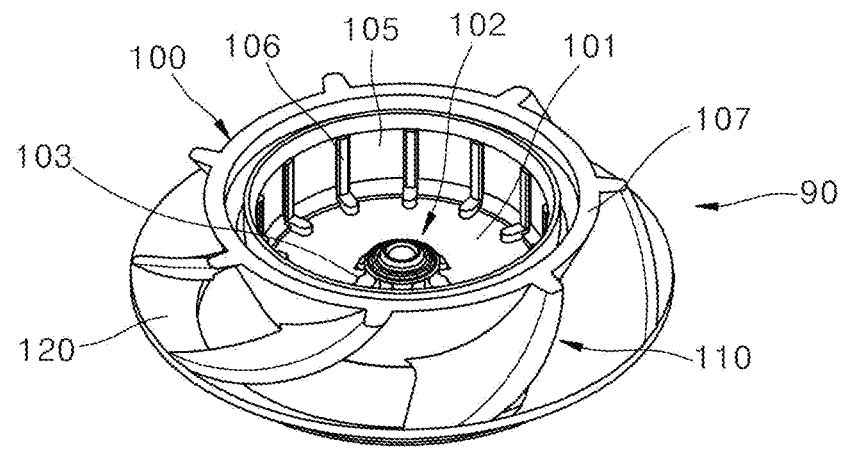
Figure 4:
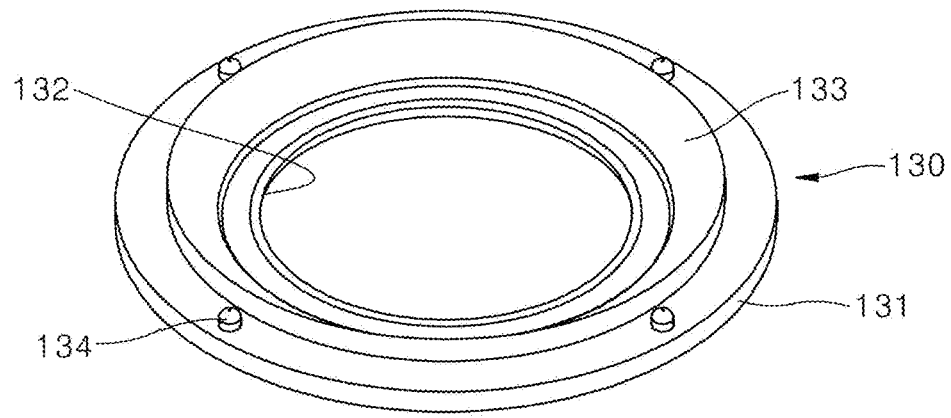
Figure 5:
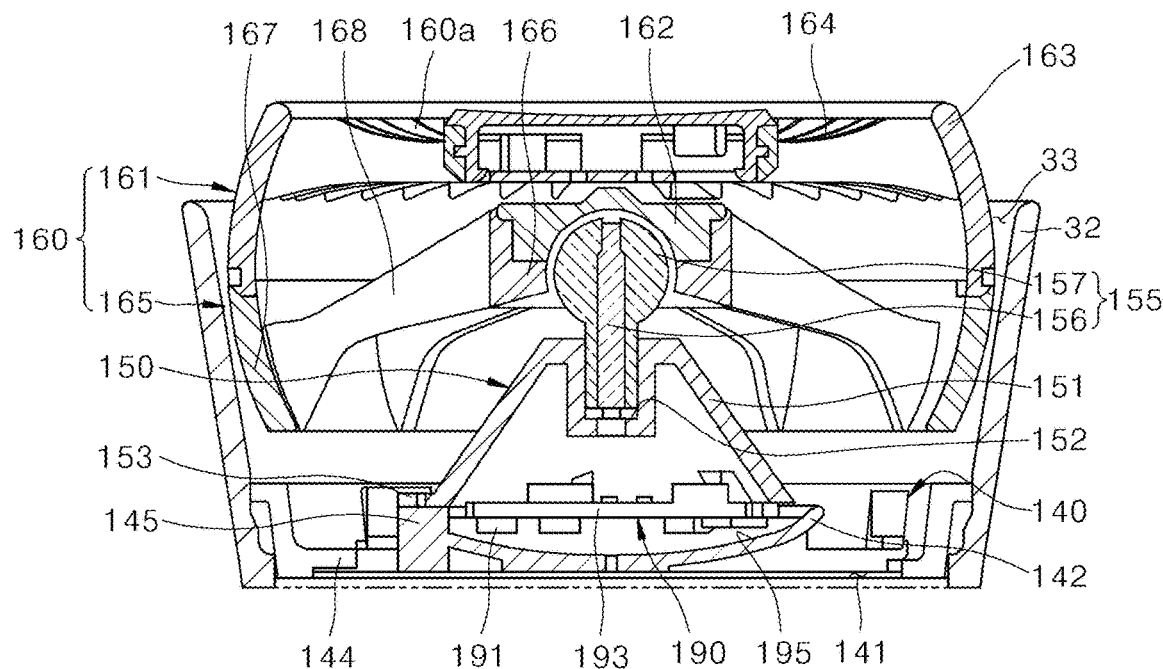
FIG. 5 is an enlarged view showing portion "V" in FIG. 2.

FIG. 3 is a perspective view of a fan module of the portable air purifier of FIG. 2. FIG. 4 is an exploded perspective view showing a state in which the fan module in FIG. 3 is disassembled. FIG. 5 is an enlarged view showing portion "V" in FIG. 2.

Referring to FIGS. 2 to 5, when a circular mixed flow fan module is used as the fan module 70, a shape of the circular mixed flow fan module may correspond to an inner shape of the first housing 10 formed into a cylinder. In this case, the first housing 10 does not have to be scaled up for fixing or fastening the fan module 70, thereby making the product compact.

Additionally, even if the fan module 70 has a size corresponding to a size of a cup holder, the portable air purifier 1 may have a size small enough to be held in the cup holder. Thus, output of the fan module 70 may be maximized within a range in which the portable air purifier 1 may be held in a structure in a vehicle.

The fan module 70 may include a fan housing 80, a fan 90, and a fan base 130. The fan housing 80 may be fixed to the inside of the first housing 10. The fan housing 80 may include a support plate 81, a connection supporter 82, and a lateral surface support 84.

The support plate 81 may be formed into a circular plate, and have a hole at a center thereof. A motor may be disposed at the center of the support plate 81, or a shaft connected to the motor may be installed in the first direction. The support plate 81 may be disposed below support modules 140, 150.

The connection supporter 82 may extend to an outside of the support plate 81 and connect to the lateral surface support 84. In this embodiment, a plurality of connection supporters 82 is disposed along a circumferential direction of the support plate 81, for example. Additionally, in this embodiment, each of the connection supporters 82 is formed into a rod, for example.

The lateral surface support 84 may be formed into a cylindrical pipe, and both vertical direction sides of the lateral surface support 84 may be open. An outside of the lateral surface support 84 may contact insides of the second case 30 and the middle case 40, and an inside of the lateral surface support 84 may connect to the plurality of connection supporters 82 respectively.

The fan 90 may be rotatably installed inside of the fan housing 80. Within the technical scope in which the fan 90 moves air toward the discharge outlet 160, the fan 90 may be implemented in various different forms.

In this embodiment, a mixed flow fan is used as the fan 90, for example; however, embodiments are not limited. A variety of fans may be applied as the fan 90 of the fan module 70 in addition to a mixed flow fan.

In this embodiment, the fan 90 may include at least one of a hub 100, a fan blade 110, or a shroud 120. The hub 100 may be disposed at a center of the fan housing 80, and implemented in various different forms within the technical scope in which the hub 100 rotates by receiving external power.

The hub 100 may be disposed at a center of the fan 90 in a radial direction thereof, and rotate together with a rotor forming the motor, and a shaft which is an output shaft of the motor. The hub 100 may include at least one of a hub plate 101, a shaft coupler 102, an inner protrusion 105, and a skirt 107.

The hub plate 101 may be formed into a circular plate parallel with the support plate 81. The hub plate 101 may be provided with the shaft coupler 102. The shaft coupler 102 may be disposed at a radial center of the hub plate 101. The shaft coupler 102 may protrude from upper and lower sides of the hub plate 101.

The shaft coupler 102 may be coupled to an end of the shaft which delivers rotation power. For example, the shaft coupler 102 and the shaft may be coupled in such a way that the shaft is inserted into the shaft coupler 102.

A first reinforcement projection 103 may be spaced at predetermined intervals along an outer circumference of the shaft coupler 102. The first reinforcement projection 103 may be disposed radially around the shaft coupler 102, and form a strap-shaped projection outside of the shaft coupler 102. Stress concentrated on the shaft coupler 102 may spread through the first reinforcement projection 103. Accordingly, structural rigidity of the shaft coupler 102 may be improved.

The inner protrusion 105 may protrude upward from the hub plate 101 to the support plate 81. In this embodiment, the inner protrusion 105 is formed in a circular arc direction along an outer edge of the hub plate 101, for example. The inner protrusion 105 may be formed into a pipe that extends in the vertical direction.

Additionally, a second reinforcement projection 106 may be disposed at predetermined intervals along an inner circumference of the inner protrusion 105. The second reinforcement projection 106 may be formed into a strap-shaped projection that extends in the vertical direction, on an inner surface of the inner protrusion 105. A lower side of the second reinforcement projection 106 may form a strap-shaped projection that extends toward the shaft coupler 102. Stress concentrated on the inner protrusion 105 may spread through the second reinforcement projection 106. Accordingly, structural rigidity of the inner protrusion 105 may be improved. In some embodiments, the rotor of the motor may be fixed to an inside of the inner protrusion 105.

The skirt 107 may protrude upward from an edge of the hub plate 101 to the support plate 81. The skirt 107 may form an inclined surface that inclines in a centrifugal direction of the hub plate 101 as the skirt 107 extends away from the hub plate 101 in the first direction. The skirt 107 may be disposed outside of the inner protrusion 105, and an inner diameter of the skirt 107 may gradually increase from a lower side to an upper side.

For example, a shape in which the hub plate 101 and the skirt 107 connect may be a truncated cone shape which has a hollow hole therein, and one side of which is open. The skirt 107 may be formed into a funnel, an upper side of which is open and the other side of which is closed by the hub plate 101.

The shroud 120 may be disposed outside of the skirt 107 in a radial direction thereof, and the shroud 120 and the skirt 107 may be connected by the fan blade 110. Further, an outer diameter of the hub 100 and an inner diameter of the shroud 120 may gradually decrease from upper sides to lower sides.

The shroud 120 may be spaced a predetermined distance apart from the hub 100 in the radial direction, and disposed outside of the hub 100 in the radial direction thereof. The shroud 120 may be spaced from the hub 100 by a distance corresponding to a radial length of the fan blade 110. Each fan blade 110 may connect between the skirt 107 included in the hub 100 and the shroud 120.

The shroud 120 may form an inclined surface that is approximately parallel with the skirt 107. In this embodiment, the skirt 107 and the shroud 120 are disposed in such a way that a gap between the skirt 107 and the shroud 120 gradually increases toward the upper side of the shroud 120, for example.

An inlet projection 121 disposed at a lower side of the shroud 120 may be formed into a ring-shaped projection, and extend from the lower side of the shroud 120 formed into a funnel in the first direction. As the inlet projection 121 is disposed inside of a bell mouth 132 described hereinafter, a whirlwind movement of air suctioned into an inlet disposed at the lower side of the shroud 120 along an outside of the shroud 120 may be prevented.

A plurality of fan blades 110 may be disposed between the skirt 107 and the shroud 120. The plurality of fan blades 110 may be spaced at regular intervals along an outer circumferential surface of the hub 10. Each of the fan blades 110 may protrude outward from the hub 100 around the hub 100 and extend in a spiral shape.

The fan blade 110 may connect to the skirt 107 of the hub 100. To allow air suctioned into the fan module 70 to flow in an oblique upward direction, the skirt 107 may form an inclined surface in the oblique upward direction.

The fan base 130 may be disposed between the filter 60 and the fan 90. An edge of the fan base 130 may have a shape corresponding to a shape of an edge of the filter 60. For example, when the filter 60 has a cylinder shape and the edge the filter 60 has a circle shape, the fan base 130 have a ring shape with a hollow hole. The fan base 130 may include a base plate 131 and the bell mouth 132.

The base plate 131 may be disposed between the filter 60 and the fan 90. The base plate 131 may be formed into a plate that extends in a ring shape, and have a hollow hole through which air moves, at a center thereof. A passage for allowing air to pass through the base plate 131 may be formed by the hollow hole of the base plate 131.

The bell mouth 132 may be provided in a ring shape at an inside of the base plate 131, which faces the hollow hole. The bell mouth 132 may have a concavely-shaped longitudinal cross section that surrounds a lower side of the inlet projection 121 of the shroud 120 and extends along a circumferential direction.

The bell mouth 132 may surround an outer circumferential surface of the hollow hole formed at the center of the base plate 131. The bell mouth 132 may form a groove which is convex downward and concave upward.

At least a portion of the bell mouth 132 may be inserted into the shroud 120 in the radial direction thereof. The bell mouth 132 may guide suction and flow at an inlet of the fan module 70, thereby contributing to improvement in suction and discharge performance of the fan module 70.

A coupling projection 134 may protrude from the base plate 131 upward. The coupling projection 134 may be fit-coupled to a fitting groove disposed at a lower end of the fan housing 80. In this embodiment, a plurality of coupling projections 134 is spaced a predetermined distance apart from one another along a circumferential direction of the base plate 131, for example.

Based on the fit coupling between the coupling projection 134 and the fan housing 80, the fan base 130 and the fan housing 80 may be coupled at a plurality of points. When the fan base 130 and the fan housing 80 are coupled as described above, the fan 90 may be rotatably installed between the fan base 130 and the fan housing 80.

A protrusion rib 133 may protrude from the base plate 131 and be disposed outside of the bell mouth 132 in a radial direction thereof. In this embodiment, the protrusion rib 133 is formed into a ring that surrounds the bell mouth 132 outside of the bell mouth 132 in the radial direction thereof, for example.

The protrusion rib 133 may be integrated with the base plate 131. More specifically, the base plate 131, the bell mouth 132, and the protrusion rib 133 may be integrated with one another.

Further, the protrusion rib 133 may be installed at a slant at an angle the same as an angle of an outer surface of the shroud 120, and a gap between the protrusion rib 133 and the shroud 120 may remain constant. The protrusion rib 133 may protrude in a way that forms an inclined surface. The inclined surface of the protrusion rib 133 may be spaced a predetermined distance apart from the shroud 120 and formed into an inclined surface parallel with the inclined surface of the shroud 120.

The sterilizer 170 may be disposed between the filter 60 and the second hosing part 50. Within the technical scope in which the sterilizer 170 irradiates light rays for sterilization to the filter 60, the sterilizer 170 may be implemented in various different forms. In this embodiment, the sterilizer 170 includes at least one of a sterilizer support 171, a holder 176, or an irradiator 180, for example.

The sterilizer support 171 may be disposed between the first housing 10 and the second housing 50, and shield the lower portion of the first housing 10. The sterilizer support 171 may include a support base 172 and a fixing edge 173.

The support base 172 may be formed into a circular plate. The support base 172 may be disposed between upper portion fixing portion 27 and the lower portion holder 54. A vertical direction position of the support base 172 in the vertical direction may be maintained by the upper portion fixing portion 27 and the lower portion holder 54.

The fixing edge 173 may protrude upward from an edge of the support base 172. When the first housing 10 and the second housing 50 are coupled, the upper portion fixing portion 27 may be coupled to an inner circumferential surface of the fixing edge 173.

That is, when the first housing 10 and the second housing 50 are coupled, the sterilizer support 171 may be fixed to the inside of the housing 10, 50 in such a way that the sterilizer support 171 is fitted among a bottom surface and a lateral surface of the upper portion fixing portion 27, an inner surface of the lower case 52, and an upper surface of the lower portion holder 54.

The sterilizer support 171, fixed to the inside of the housing 10, 50 as described above, may function as a shield between the first housing 10 and the second housing 50. That is, the sterilizer support 171 may serve as a blocking wall that blocks air suctioned into the first housing 10 through the inlet 22 from moving to the second housing 50. Accordingly, an amount of air suctioned through the inlet 22 and then flowing to the fan module 70 may increase, thereby effectively improving air purification performance of the portable air purifier 1.

The holder 176 may protrude upward from a radial center of the sterilizer support 171. Within the technical scope in which the holder 176 supports a lower portion of the irradiator 180, the holder 176 may be implemented in various different forms.

Additionally, the holder 176 may be disposed at a radial center of the inlet 22, and a transverse cross section of the holder 176 may have a circle shape. The holder 176 may reduce friction between the holder 176 and air.

In this embodiment, the holder 176 includes a holder pillar 177 and a holder plate 178, for example. The holder pillar 177 may be formed into a pillar that protrudes upward from a center of the sterilizer support 171. For example, the holder pillar 177 may be formed into a cylinder, a circular cone, or a truncated cone. In this embodiment, the holder pillar 177 is formed into a truncated cone having a transverse cross section gradually narrowed from a lower side toward an upper side, for example.

A transverse cross section of the sterilizer support 171 installed to sterilize the filter 60 may have a circle shape. Air suctioned through the inlet 22 may flow to an upper side at which the filter 60 is installed, while rotating an outside of the holder pillar 177 spirally. That is, the sterilizer 170 may be disposed at a central portion of the first housing 10, and air suctioned through the inlet 22 may move upward while moving around an outer circumference of the sterilizer 170. Accordingly, flow resistance caused by the sterilizer 170 may decrease.

Rotational centers of the holder 176 and the fan 90, and a holder body 151 may be disposed on a same straight line in a perpendicular direction. Accordingly, resistance against a flow of air moving from a lower side to an upper side may decrease, thereby enable the air to flow more smoothly. Thus, air purification performance of the portable air purifier 1 may be improved.

The holder plate 178 may be formed into a plate that is disposed in the horizontal direction at an upper side of the holder pillar 177. The irradiator 180 may be disposed at an upper side of the holder plate 178. To prevent light rays irradiated from the irradiator 180 from moving downward, the holder plate 178 may have a cross section the same as or greater than a cross section of the irradiator 180.

The irradiator 180 may be mounted onto an upper side of the holder 176, and irradiate light rays for sterilization toward the filter 60. Within the technical scope in which the irradiator 180 is disposed at a position higher than or the same as an upper end of the inlet 22, the irradiator 180 may be implemented in various different forms. In this embodiment, the irradiator 180 includes a printed circuit board (PCB) 181, and a light source for sterilization 182, for example.

The printed circuit board 181 may be disposed at an upper side of the holder plate 178, and the light source for sterilization 182 configured to irradiate light rays for sterilization may be disposed at an upper side of the printed circuit board 181. The light source for sterilization 182 may be a UVC LED, and a variety of sterilization devices or a variety of light sources for sterilization may be used within the technical scope in which the light source for sterilization 182 sterilizes germs in the filter 60.

The light source for sterilization 182 of the sterilizer 170 may be disposed at an upper side of the inlet 22. Accordingly, light rays for sterilization irradiated from the light source for sterilization 182 are less likely to leak out of the first housing 10 through the inlet 22.

Figure 6:
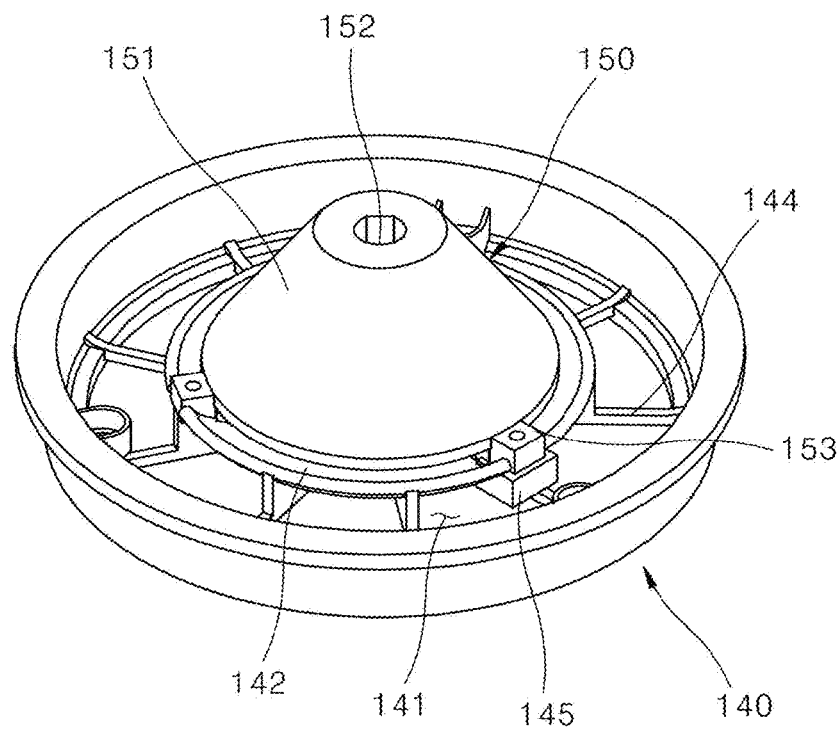
FIG. 6 is a perspective view of a support module of FIG. 5.
Figure 7:
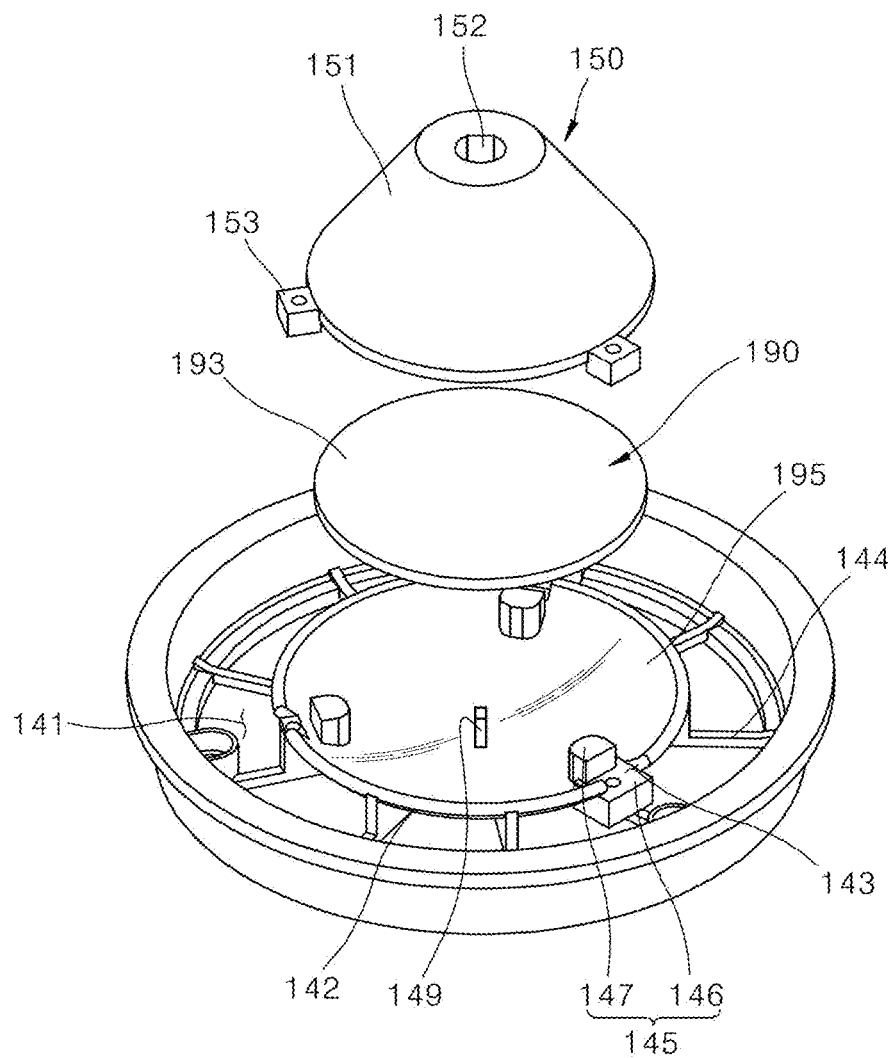
FIG. 7 is an exploded perspective view showing a state in which the support module and a lighting portion in FIG. 5 are disassembled.
Figure 8:
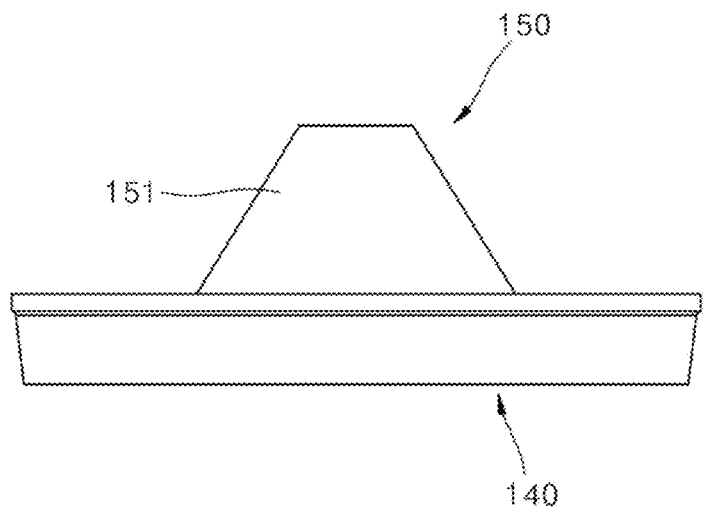
FIG. 8 is a front view of the support module of FIG. 5.
Figure 9:
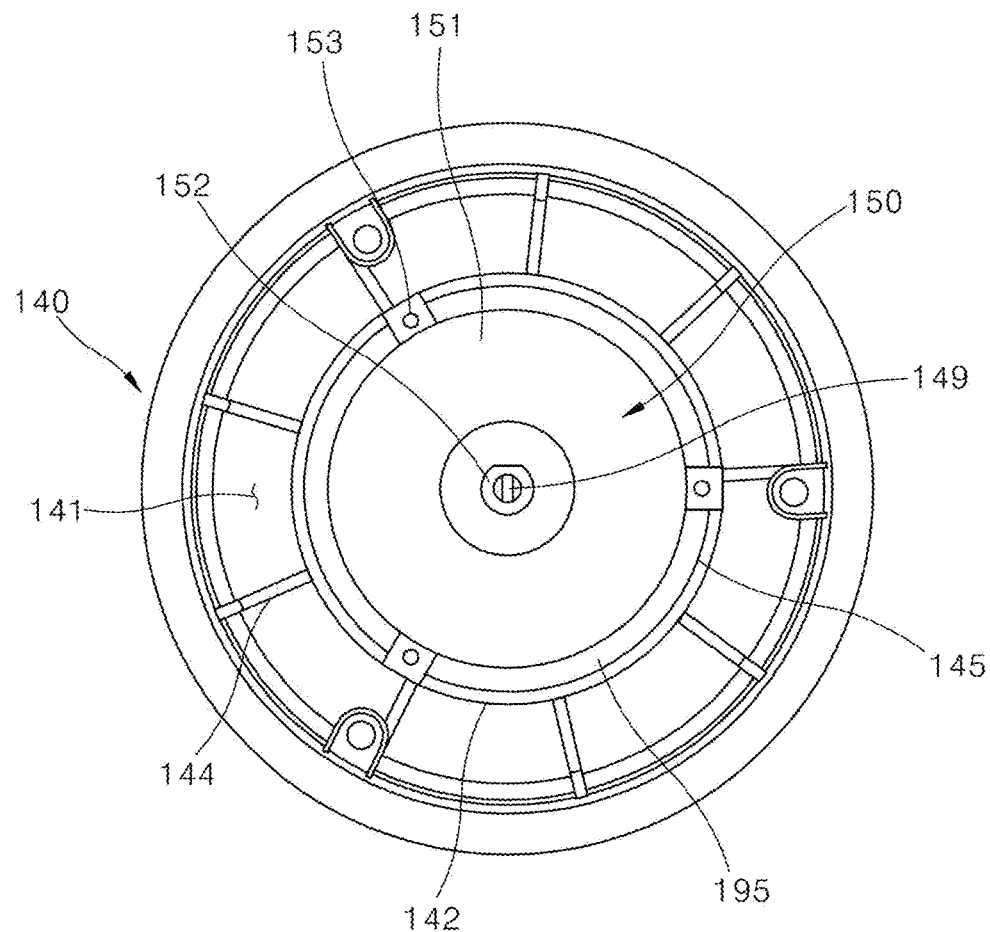
FIG. 9 is a plan view of the support module of FIG. 5.
Figure 10:
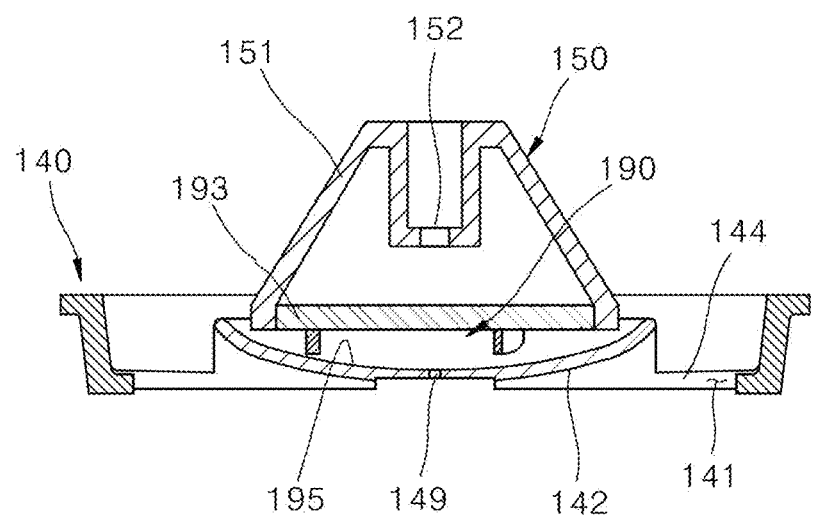
FIG. 10 is a cross-sectional view, taken along line "X-X" in FIG. 6.

FIG. 6 is a perspective view of a support module of FIG. 5. FIG. 7 is an exploded perspective view showing a state in which the support module and a lighting portion in FIG. 5 are disassembled. FIG. 8 is a front view showing the support module of FIG. 5. FIG. 9 is a plan view of the support module of FIG. 5. FIG. 10 is a cross-sectional view, taken along line "X-X" in FIG. 6.

Referring to FIGS. 5 to 8, the support modules 140, 150 may be disposed between the fan module 70 and the discharge outlet 160 and support the discharge outlet 160. The support modules 140, 150 may include fan cover 140 and support 150.

The fan cover 140 may be disposed between the fan module 70 and the discharge outlet 160. The fan cover 140 may be provided with an air discharge outlet 141. The air discharge outlet 141 may be formed in such a way that a portion of the fan cover 140 is penetrated or cut in the vertical direction. The air discharge outlet 141 may form a passage that connects the fan 90 and the discharge outlet 160, on the fan cover 140.

In this embodiment, the fan cover 140 includes a shielding plate 142 and a guide vane 144, for example. The shielding plate 142 may be disposed over the fan 90, that is, at a discharge side of the fan 90. In this embodiment, the shielding plate 142 is disposed at a central portion of the fan cover 140, for example. The shielding plate 142 may be disposed in front of the hub 100 and cover the hub 100.

Like the shielding plate 142, the guide vane 144 may be disposed over the fan 90. In this embodiment, the guide vane 144 is disposed between an inner circumferential surface of the fan cover 140 surrounding the shielding plate 142 outside of the shielding plate in a lateral direction thereof, and the shielding plate 142, for example.

A plurality of guide vanes 144 may be spaced a predetermined distance apart from one another between the inner circumferential surface of the fan cover 140 and the shielding plate 142 along a circumferential direction of the shielding plate 142. Each of the guide vanes 144 may extend from the shielding plate 142 in the centrifugal direction. The guide vanes 144 may serve as a connection structure that allows the shielding plate 142 disposed at a central portion of the air discharge outlet 141 to be supported by the fan cover 140.

The shielding plate 142 is needed to cover a portion of the hub 100 of the fan 90. However, to ensure passage of air discharged from the fan 90, the shielding plate 142 should not cover the air discharge outlet 141 completely. Thus, the shielding plate 142 may have a size less than a size of the air discharge outlet 141 to cover only a portion of the air discharge outlet 141, and the guide vane 144 may connect the inner circumferential surface of the fan cover 140 and the shielding plate 142.

The guide vanes 144 may guide a discharge direction of air discharged from the fan 90 in addition to supporting the shielding plate 142. The plurality of guide vanes 144 may be disposed on the air discharge outlet 141 and spaced a predetermined distance apart from one another along the circumferential direction of the shielding plate 142.

The support 150 may be disposed between the fan cover 140 and the second discharge opening 160a. The support 150 may be supported by the fan cover 140 and support the discharge outlet 160. In this embodiment, the support 150 includes holder body 151 and a support rod 155, for example.

The holder body 151 may be disposed between the shielding plate 142 and the discharge outlet 160. The holder body 151 may be coupled to the shielding plate 142 in an upper portion of the shielding plate 142, and support the support rod 155 at a lower portion of the support rod 155.

In this embodiment, the holder body 151 has a shape including a solid figure that have a bottom surface that forms a lower end edge of the holder body 151 and is formed into a circle, and a lateral surface that forms a lateral wall of the holder body 151 and is formed into a curved surface narrowed toward an upper portion of the holder body 151, for example.

For example, the holder body 151 may be formed into a truncated cone having a width that narrows toward an upper portion. The holder body 151 may have an accommodating space therein, and the accommodating space in the holder body 151 may be open downward. The lower end edge of the holder body 151 formed into a truncated cone may have a circle shape.

The support rod 155 may be coupled to the holder body 151 to support the discharge outlet 160 in a posture changeable manner. In this embodiment, the support rod 155 includes a body 156 and a ball 157, for example.

The body 156 may be a circular rod and may be coupled to the holder body 151. For example, a fitting groove 152 which is concave downward may be formed at an upper end of the holder body 151, and the body 156 may be coupled to the holder body 151 by being fitted into the fitting groove 152. The support rod 155 and the holder body 151 may be coupled using a variety of methods, such as screw fastening or pin fastening or an adhesive, for example.

The ball 157 may be disposed at an upper end of the body 156. The ball 157 may be formed into a sphere, and coupled to an inside of the discharge outlet 160 and rotatably support the discharge outlet 160. The support rod 155 and the holder body 151 may be fixed using a variety of fixing methods, such as screw fastening or pin fastening or an adhesive, for example.

The discharge outlet 160 may be rotatably disposed at the first housing 10. Within the technical scope in which the discharge outlet 160 adjusts a discharge direction of air having passed through the fan module 70, the discharge outlet 160 may be implemented in various different forms. In this embodiment, the discharge outlet 160 is rotatably installed at the support rod 155 of the support 150, for example. The discharge outlet 160 may effectively adjust a discharge direction of purified air while smoothly rotating at a discharge side of the portable air purifier 1.

The discharge outlet 160 may be disposed on the support 150. A single member may be provided as the discharge outlet 160 or a plurality of components combined may be provided as the discharge outlet 160. In this embodiment, the discharge outlet 160 includes a first discharge outlet 161, and a second discharge outlet 165, for example.

The first discharge outlet 161 may be disposed in upper portions of the support 150 and the second discharge outlet 165. Within the technical scope in which the first discharge outlet 161 is provided with a plurality of vanes 164 configured to guide discharge of air, the first discharge outlet 161 may be implemented in various different forms. In this embodiment, the first discharge outlet 161 includes a first discharge core 162, a first discharge body 163, and a vane 164, for example.

The first discharge core 162 may be disposed over the holder body 151. The first discharge core 162 may surround the ball 157 of the support rod 155, formed into a sphere. The first discharge core 162 may be formed in such a way that surrounds an upper half of the ball 157.

The first discharge body 163 together with a second discharge body 167 described hereinafter may form an exterior of a lateral surface of the discharge outlet 160. The first discharge body 163 may be formed into a ring that surrounds an outside of the first discharge core 162. Additionally, an outer surface of the first discharge body 163 may be formed into a shape including a curved surface.

Both vertical direction sides of the first discharge body 163 may be open, and the first discharge body 163 may have a space for accommodating the first discharge core 162, and a portion of the support 150, for example, therein. Air discharged from the upper portion of the fan module 70 may pass through the fan cover 140 and then pass through a path formed in the first discharge body 163. The air having passed through the path formed in the first discharge body 163 may be discharged from the upper portion of the discharge outlet 160 through the second discharge opening 160a formed in an upper portion of the first discharge body 163.

A plurality of vanes 164 may be disposed between the first discharge core 162 and the first discharge body 163. Each of the vanes 164 may connect the first discharge core 162 and the first discharge body 163. The vanes 164 may be disposed on the second discharge opening 160a, and surround the first discharge core 162 in a circumferential direction. The plurality of vanes 164 may be spaced a predetermined distance apart from one another along the circumferential direction of the first discharge core 162, and air may be discharged through gaps among the vanes 164. As the first discharge core 162 and the first discharge body 163 are connected to each other by the plurality of vanes 164, the first discharge core 162, the first discharge body 163, and the vanes 164 may move as a single body.

The second discharge outlet 165 may be disposed between the holder body 151 and the first discharge outlet 161. Within the technical scope in which the second discharge outlet 165 together with the first discharge outlet 161 is coupled to the support rod 155 and rotates around the ball 157 of the support rod 155, the second discharge outlet 165 may be implemented in various different forms. In this embodiment, the second discharge outlet 165 includes a second discharge core 166, second discharge body 167, and a discharge supporter 168, for example.

The second discharge core 166 may be disposed between the holder body 151 and the first discharge outlet 161. The second discharge core 166 together with the first discharge core 162 may surround the ball 157 of the support rod 155, formed into a sphere. The second discharge core 166 may be formed in such a way that it surrounds a lower half of the ball 157.

The second discharge body 167 together with the first discharge body 163 may form an exterior of a lateral surface of the discharge outlet 160. The second discharge body 167 may be formed into a ring that surrounds an outside of the second discharge core 166. Additionally, an outer surface of the second discharge body 167 may be formed into a shape including a curved surface.

Both vertical direction sides of the second discharge body 167 may be open, and the second discharge body 167 may have a space for accommodating the second discharge core 166, and a portion of the support 150, for example, therein. Air discharged from the upper portion of the fan module 70 may pass through the fan cover 140 and then pass through paths formed in the second discharge body 167 and the first discharge body 163. The air having passed through the paths formed in the second discharge body 167 and the first discharge body 163 may be discharged from the upper portion of the discharge outlet 160 through the second discharge opening 160a formed in the upper portion of the first discharge body 163.

A plurality of discharge supporters 168 may be disposed between the second discharge core 166 and the second discharge body 167. Each of the discharge supporters 168 may connect the second discharge core 166 and the second discharge body 167. As the second discharge core 166 and the second discharge body 167 are connected to each other by the plurality of discharge supporters 168, the second discharge core 166, the second discharge body 167, and the discharge supporters 168 may move as a single body.

Additionally, the first discharge core 162 and the second discharge core 166 may be coupled to each other, with the ball 157 of the support rod 155 therebetween, and the first discharge body 163 and the second discharge body 167 may be coupled to each other in the vertical direction. Thus, the first discharge outlet 161 and the second discharge outlet 165 may move as a single body.

Figure 11:
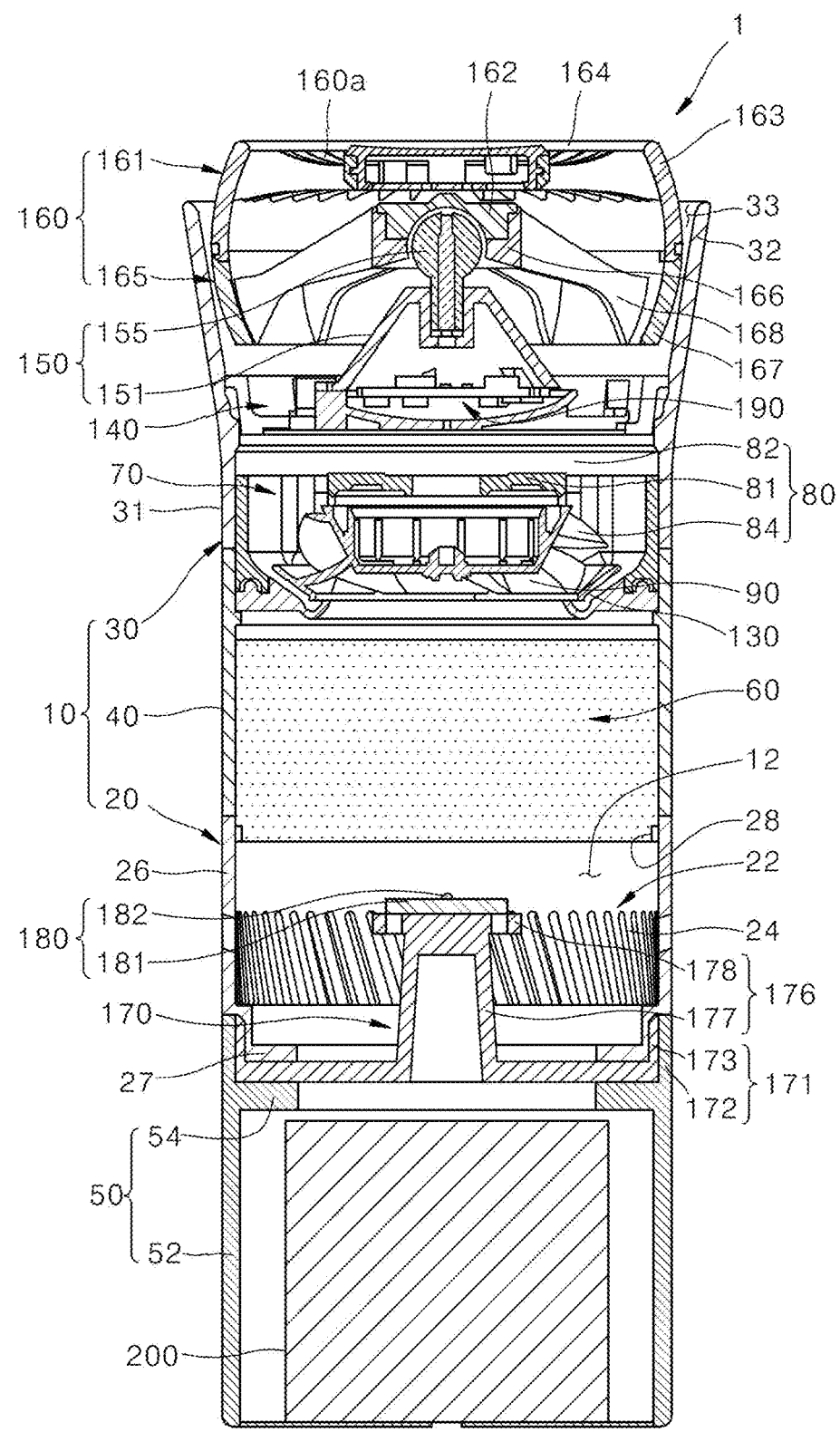
FIG. 11 is a view showing an air flow in the portable air purifier of FIG. 2.
Figure 12:
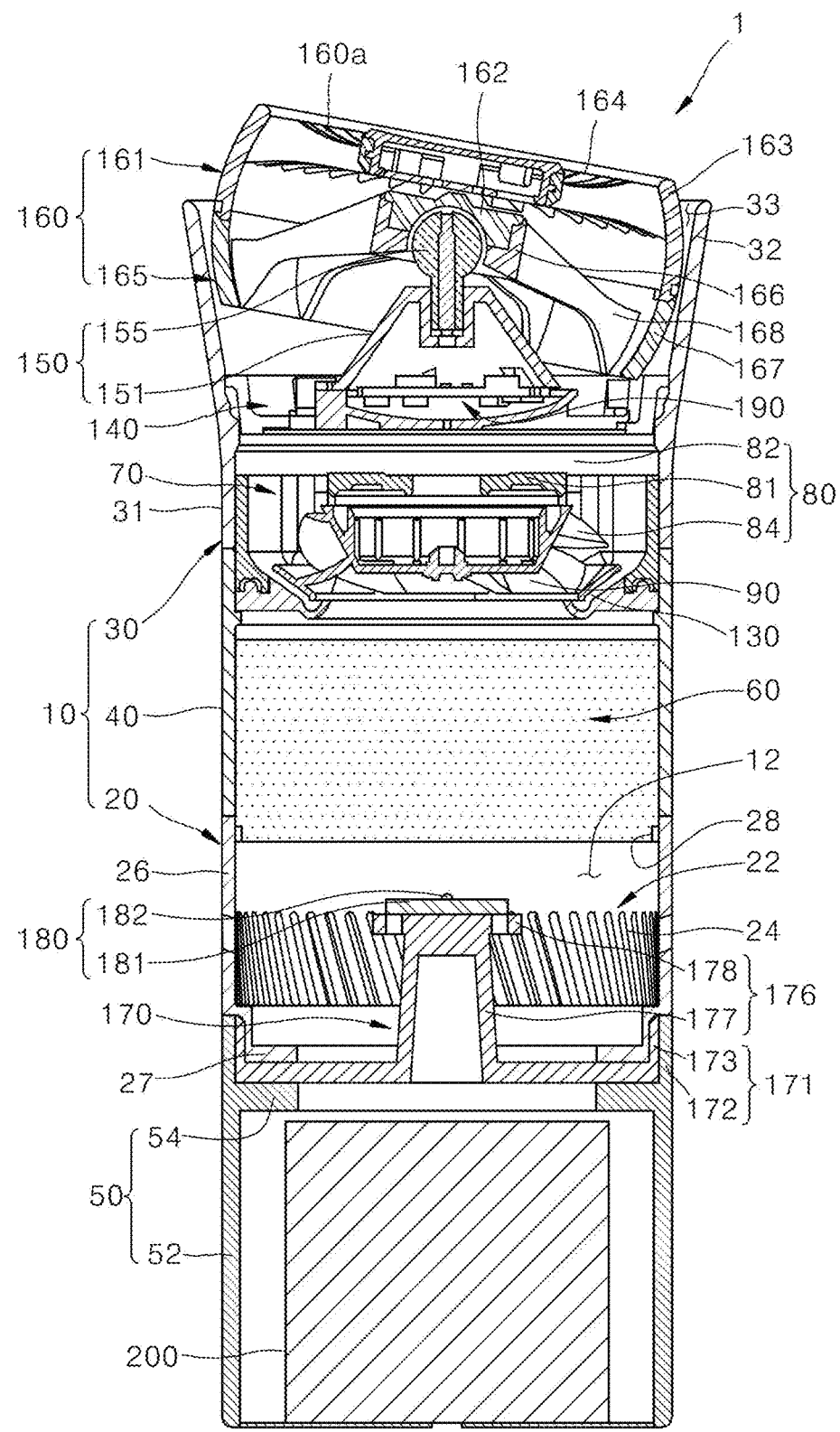
FIG. 12 is a view showing a state in which a discharge outlet of the portable air purifier in FIG. 11 is rotated.

FIG. 11 is a view showing an air flow in the portable air purifier of FIG. 2. FIG. 12 is a view showing a state in which a discharge outlet of the portable air purifier in FIG. 11 is rotated.

Hereafter, an air flow of the portable air purifier 1 according to an embodiment is described with reference to FIGS. 11 and 12.

Referring to FIG. 11, as a result of operation of the fan module 70, air outside of the portable air purifier 1 may be suctioned into the portable air purifier 1. In this case, the air, suctioned into the portable air purifier 1 through the suction opening 24 installed in an inclined shape, may flow upward while forming a spiral flow that rotates around the outer circumference of the sterilizer support 171.

The air moving upward in the portable air purifier 1 may pass through the filter 60, and in this process, the filter 60 may filter physical particles, such as dust/fine dust/ultra-fine dust, for example, chemical substances, such as odorant particles/harmful gases, for example, and microorganisms, such as germs/viruses, for example, included in the air. As the filter 60 and the fan module 70 are disposed on a straight line in the vertical direction, flow loss may be minimized, and air may be effectively suctioned and filtered.

The air having passed through the filter 60, that is, purified air, may be suctioned into the fan module 70. A flow of air may be guided by the bell mouth 132, thereby enabling the air to be suctioned into the fan module 70 effectively.

The air suctioned into the fan module 70 may be discharged from the upper side of the fan module 70. The air discharged from the upper side of the fan module 70 may be discharged in a mixed flow direction. Herein, the mixed flow direction may be defined as an upward diagonal line direction.

Air suctioned into the central portion of the lower side of the fan module 70 may be discharged upward from the fan module 70. A flow of the air discharged upward may be guided by the fan cover 140. For example, a flow of the air discharged from the fan module 70 in the mixed flow direction may be guided in a direction eccentric to a front while being guided by the guide vane 144 included in the fan cover 140.

The air, discharged from the upper sides of the fan module 70 and the fan cover 140 as described above, may pass through the discharge outlet 160, that is, through a lower open portion of the discharge outlet 160 and then be discharged from the upper side of the discharge outlet 160 through the second discharge opening 160a.

The discharge outlet 160 may rotate within a range of predetermined angles. As a posture of the discharge outlet 160 changes, a direction of discharge of air through the discharge outlet 160 may be adjusted.

For example, when the discharge outlet 160 is rotated to change its posture as illustrated in FIG. 12, in a state in which the second discharge opening 160a of the discharge outlet 160 faces an upper portion in the perpendicular direction, a discharge direction of air facing the upper portion in the perpendicular direction may change to an inclined direction in response to the change in the posture of the discharge member 160.

Figure 13:
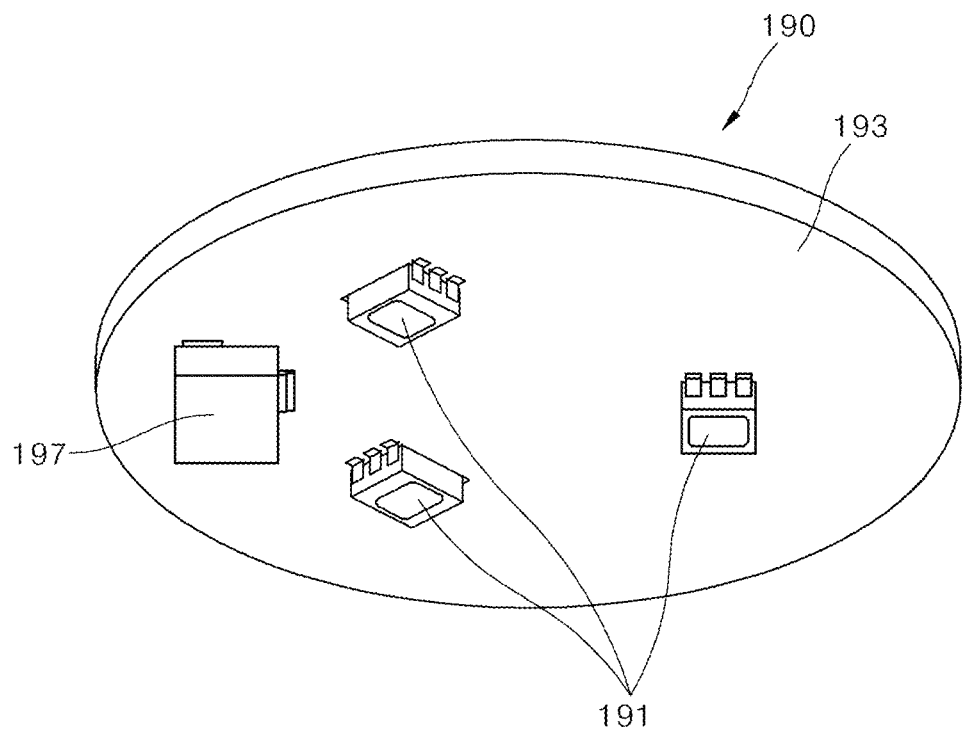
FIG. 13 is a bottom perspective view of a lighting portion according to an embodiment.

FIG. 13 is a bottom perspective view of a lighting portion according to an embodiment. Referring to FIGS. 5, 9 and 13, the portable air purifier 1 according to an embodiment may further include lighting portion 190. The lighting portion 190 may be installed in the support modules 140, 150 and irradiate light rays. The lighting portion 190 may be disposed in a space surrounded by the fan cover 140 and the support 150.

Within the technical scope in which at least a portion of light rays irradiated from the lighting portion 190 is emitted out of at least one of the housing 10, 50 or the discharge outlet 160 through at least one of the first discharge opening 33 and the second discharge opening 160a, the lighting portion 190 may be implemented in various different forms. In this embodiment, the lighting portion 190 includes a light source 191, a board 193, and a reflector 195, for example.

The light source 191 may be configured to irradiate light rays to the lower portion of the support 150. The light source 191 may be disposed in a space surrounded by the fan cover 140 and the support 150, more specifically, a space surrounded by the shielding plate 142 and the holder body 151.

The light source 191 may be disposed over the shielding plate 142 and configured to irradiate light rays toward the shielding plate 142 dispose below the light source 191. In this embodiment, the light source 191 includes a light emitting diode (LED) that irradiates light rays, for example. The light source 191 may be mounted onto and fixed to the board 193.

The board 193 may be provided in the form of a printed circuit board. The board 193 may be provided in the form of a rigid printed circuit board (PCB) or a flexible printed circuit board (FPCB).

The reflector 195 may be disposed below the light source 191. The reflector 195 may reflect light rays irradiated from the light source 191 toward the discharge and discharge openings 33, 160a. The reflector 195 may have a shape including a curved surface which is concave downward.

In this embodiment, while the reflector 195 has a shape including at least a portion of an oval, the reflector 195 has a shape in which a portion, located on a perpendicular reference line passing through a horizontal center, more specifically, a center of the housing in the vertical direction, is disposed in a lowermost position.

In this embodiment, the reflector 195 is disposed at the shielding plate 142, for example. The shielding plate 142 may have a shape including a portion of an oval, which is concave downward, and the reflector 195 may be formed on the shielding plate 142. For example, the reflector 195 may be formed in such a way that the reflector 195 includes one lateral surface of the shielding plate 142, facing the light source 191.

For example, one lateral surface of the shielding plate 142, facing the light source 191, may the reflector 195. As another example, one lateral surface of the shielding plate 142, facing the light source 191, may be surface-coated to reflect light, and the surface-coated lateral surface of the shielding plate 142 may be the reflector 195. The reflector 195 may be implemented in various different forms, as described above.

The light source 191 configured to irradiate light rays toward the reflector 195 over the reflector 195 may be disposed in a space surrounded by the reflector 195 and the holder body 151, and may be disposed closer to a focal point of an oval in which at least a portion has a shape including the shape of the reflector 195 than to a center of the oval.

For example, a plurality of light sources 191 may be disposed over the reflector 195, and each of the light sources 191 may be disposed closer to the edge of the reflector 195 than to the radial center of the reflector 195. In this embodiment, three light sources 191 are spaced a predetermined distance apart from the radial center of the reflector 195 along the circumferential direction of the shielding plate 142, for example.

When the light sources 191, configured to irradiate light rays toward the reflector 195 formed into a curved surface which is concave downward, are disposed as described above, the light rays irradiated from the light sources 191 may be reflected mostly in a position closer to the edge of the reflector 195, and the light rays reflected tend to emit in an almost perpendicular direction rather than spread laterally.

Additionally, as the reflector 195 is formed into an oval, the reflector 195 may evenly reflect the light rays irradiated from the light sources 191, thereby ensuring improvement in light uniformity of light provided by the lighting portion 190 effectively.

In this embodiment, the shielding plate 142 provided with the reflector 195, and the holder body 151 may be disposed in the vertical direction. A lower end edge of the holder body 151, facing the shielding plate 142, may be disposed inside of the shielding plate 142 in a lateral direction thereof, namely, in the radial direction thereof.

For example, an upper end edge of the shielding plate 142 formed into a shape including a curved surface which is concave downward, and a lower end edge of the holder body 151 formed into a truncated cone may have a circle shape taking a same axis as a center, respectively.

A radius of the upper end edge of the shielding plate 142 may be greater than a radius of the lower end edge of the holder body 151. Accordingly, a ring-shaped gap may be formed between the upper end edge of the shielding plate 142 and the lower end edge of the holder body 151.

The ring-shaped gap may form a passage allowing light rays reflected upward by the reflector 195 to be emitted out of the support 150, on the support modules 140, 150. That is, light rays irradiated from the light source 191 downward may be reflected upward by the reflector 195 and then emitted out of the support modules 140, 150 through the ring-shaped gap formed between the upper end edge of the shielding plate 142 and the lower end edge of the holder 151.

Figure 14:
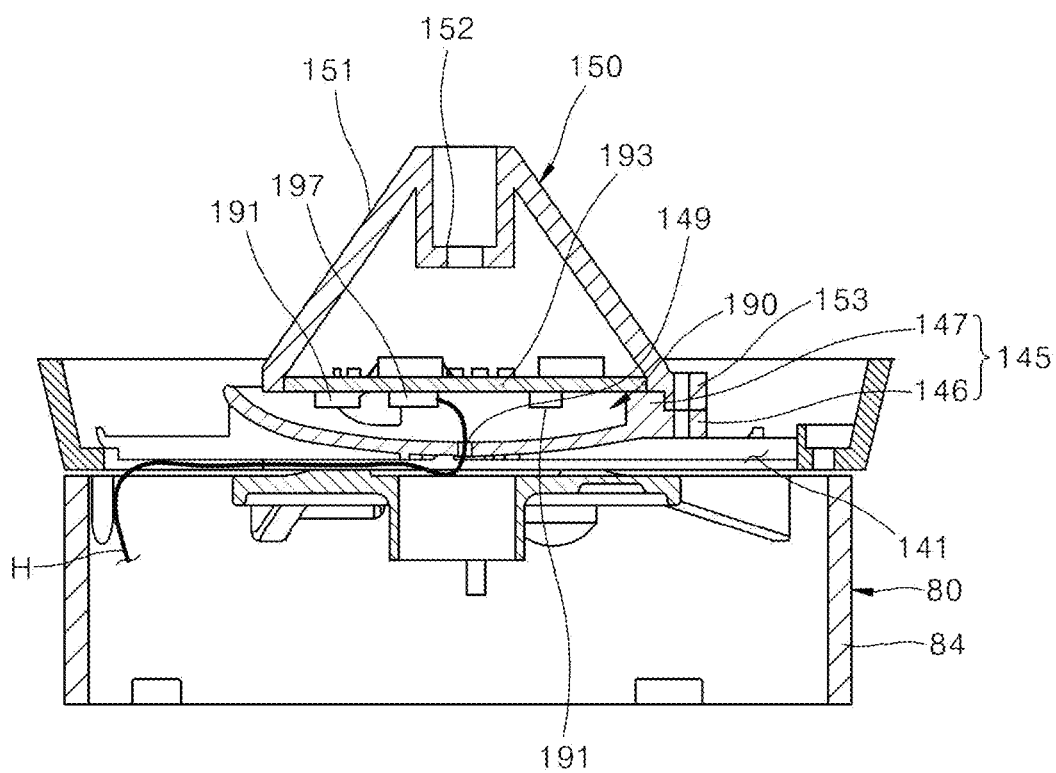
FIG. 14 is a cross-sectional view showing a state in which the lighting portion in FIG. 13 connects to an electric wire.

FIG. 14 is a cross-sectional view showing a state in which the lighting portion in FIG. 13 connects to an electric wire. Referring to FIGS. 2 to 4, 13 and 14, the board 193 onto which the light source 191 is mounted may be fixed between the shielding plate 142 and the holder body 151, on the light source 191. The board 193 may be fixed, based on coupling between the holder body 151 and the shielding plate 142 with the board 193 between the holder body 151 and the shielding plate 142.

For the coupling between the holder body 151 and the shielding plate 142, the support 150 may be provided with a first mount 153, and the fan cover 140 may be provided with a second mount 145. The first mount 153 may protrude from the lower end edge of the holder body 151. The first mount 153 may protrude from the lower end edge of the holder body 151 in the centrifugal direction and the downward direction. In this embodiment, the first mount 153 is formed into a block having a hollow hole which is elongated in the vertical direction, for example.

The support 150 may be provided with a plurality of first mounts 153. The plurality of first mounts 153 may be spaced a predetermined distance apart from one another along a circumferential direction of the lower end edge of the holder body 151. In this embodiment, three first mounts 153 are arranged at the lower end of the holder body 151 along the lower end edge thereof, for example.

The second mount 145 disposed at the shielding plate 142 may be coupled to the first mount 153. The shielding plate 142 may be provided with a plurality of second mounts 145. The plurality of second mounts 145 may be spaced a predetermined distance apart from one another along a circumferential direction of the upper end edge of the shielding plate 142.

In this embodiment, three second mounts 145 are arranged at the upper end of the shielding plate 142 along the upper end edge thereof, for example. The plurality of second mounts 145 may be disposed in positions that overlap positions of the first mounts 153, disposed at the support 150, in the vertical direction. Each of the second mounts 145 may include an outer projection 146 and an inner projection 147.

The outer projection 146 may be disposed near the edge of the shielding plate 142. The outer projection 146 may protrude from the edge of the shielding plate 142 in the centripetal direction thereof and protrude upward from the bottom surface of the curved-surface shape of the shielding plate 142 while protruding from the shielding plate 142. For example, the outer projection 146 may be formed into a block having a hollow hole which is elongated in the vertical direction.

An upper surface of the outer projection 146 may form a flat surface, and a fitting hole 143 may be formed around the outer projection 146. The fitting hole 143 may be formed in such a way that a partial area of the edge of the shielding plate 142, close to the outer projection 146, is cut. A circumferential width of the fitting hole 143 may correspond to a circumferential width of the outer projection 146. The edge of the shielding plate 142 and the upper surface of the outer projection 146 may form a same surface, in a portion in which the fitting hole 143 is formed.

A lower surface of the first mount 153 may contact an upper surface of the outer projection 146 to couple the first mount 153 and the second mount 145. In this case, hollow holes of the first mount 153 and the outer projection 146 may serve as fastening holes. The first mount 153 and the second mount 145 may be coupled in such a way that a fastening member, such as a screw, for example, is fastened to the first mount 153 and the outer projection 146 through the fastening hole.

The inner projection 147 may be disposed further inward than the outer projection 146 in the lateral direction of the shielding plate 142, in other words, further inward than the outer projection 146 in the radial direction of the shielding plate 142, while being disposed near the outer projection 146. The inner projection 147 may support the first mount 153 coupled to the outer projection 146 inside of the shielding plate 142 in the radial direction thereof.

The inner projection 147 may protrude further upward than the outer projection 146 while protruding from the shielding plate 142. For example, the inner projection 147 may protrude from the outer projection 146 in the centripetal direction of the shielding plate 142, and while protruding upward from the bottom surface of the curved-surface shape of the shielding plate 142, protrude further upward than the outer projection 146.

The fitting hole 143 and the inner projection 147 may guide the first mount 153 and the outer projection 146 into a position in which the first mount 153 and the outer projection 146 are coupled. That is, the fitting hole 143 may guide the first mount 153 into a position of the first mount 153 in the circumferential direction of the shielding plate 142, and the inner projection 147 may guide the first mount 153 into a position of the first mount 153 in the radial direction of the shielding plate 142.

For example, the first mount 153 may be fitted into the fitting hole 143 from the upper portion of the shielding plate 142 to the lower portion thereof. As the first mount 153 is fitted into the fitting hole 143, positions of the first mount 153 and the outer projection 146 are aligned with each other in the circumferential direction of the shielding plate 142. In this way, the position of the first mount 153 for coupling between the first mount 153 and the second mount 145 may be guided. Additionally, when the first mount 153 is fitted into the fitting hole 143 as described above, an inner surface of the first mount 153 may interfere with an outer surface of the inner projection 147, and the position of the first mount 153 may be guided in the radial direction of the shielding plate 142.

The first mount 153 may be formed into a projection that protrudes downward from the lower end of the holder body 151 by a thickness that forms a sufficiently wide gap between upper end edges of the reflector 195 and the shielding plate 142 and the lower end edge of the holder body 151 when the first mount 153 is coupled to the second mount 145. Additionally, the first mount 153 may contribute to improving rigidity of the holder body 151.

As described above, the board 193 may be fixed between the shielding plate 142 and the holder body 151. The coupling between the first mount 153 and the second mount 145 may lead to coupling between the support 150 and the fan cover 140, more specifically, coupling between the holder body 151 and the shielding plate 142, and coupling between the holder body 151 and the shielding plate 142 may lead to fixation of the board 193 between the shielding plate 142 and the holder body 151.

In this embodiment, an upper surface of the inner projection 147 may be a flat surface, and the board 103 may be mounted onto the upper surface of the inner projection 147. When the first mount 153 and the second mount 145 are coupled, and accordingly, the shielding plate 142 and the holder body 151 are coupled, the lower end edge of the holder body 151 may limit a lateral movement of the board 193 while surrounding the board 193 from the outside in the radial direction of the shielding plate 142.

Additionally, when the shielding plate 142 and the holder body 151 are coupled as described above, a tapered lateral wall of the holder body 151 may limit an upward movement of the board 193, on the board 193. That is, the board 193 may be fixed in such a way that a lower portion of the board 193 is supported by the inner projection 147, a radial outside of the board 193 is surrounded by the lower end edge of the holder body 151, and an upward movement of the board 193 is limited by the lateral wall of the holder body 151.

The inner projection 147 may maintain the gap between the light source 191 and the reflector 195 constant while supporting the board 193 thereunder, and help to improve rigidity of the fan cover 140 including the shielding plate 142. Additionally, the inner projection 147 may protrude in the centripetal direction of the shielding plate 142, and be formed into a shape having a curved surface which is convex in the centripetal direction of the shielding plate 142. That is, a lateral surface of the inner projection 147 protruding in the centripetal direction of the shielding plate 142 may be rounded. Accordingly, when light irradiated from the light source 191 or light reflected by the reflector 195 bumps into the inner projection 147, reflection of light may occur such that the light is reflected toward the edge of the shielding plate 142.

The board 193 onto which the light source 191 is mounted may connect to at least one of the controller including a PCB and the battery 200 through an electric wire H. To form a passage allowing the electric wire H connected to the board 193 to pass through the shielding plate 142, the shielding plate 142 may be provided with a passage hole 149.

The passage hole 149 may be formed in such a way that it passes through the shielding plate 142 in the vertical direction. The electric wire H connected to the board 193 may pass through the shielding plate 142 through the passage hole 149 and be withdrawn from the lower portion of the fan cover 140.

The electric wire H having passed through the shielding plate 142 through the passage hole 149 may be withdrawn from a space between the fan cover 140 and the fan housing 80, more specifically, a space between the shielding plate 142 and the support plate 81. The electric wire H may extend to the lateral surface support 84 along a path formed by the connection supporter 82, and extend along the inner surface of the housing 10, 50 to connect to at least one of the controller or the battery 200 disposed in the second area B.

The passage hole 149 may be disposed closer to the center of the oval forming the shielding plate 142 than to the focal point of the oval. In this embodiment, the passage hole 149 is disposed at the radial center of the shielding plate 142, for example.

Light, irradiated from the light source 191 and then reflected upward by the reflector 195, may be emitted upward through the gap between the edge of the shielding plate 142 and the edge of the holder body 151. That is, light may be emitted out of the support modules 140, 150 through the outer edge of the support modules 140, 150 rather than the radial center of the support modules 140, 150.

Accordingly, light irradiated to a portion adjacent to the edge of the shielding plate 142 from the light source 191 may be mostly emitted through the outer edge of the support modules 140, 150, and light irradiated to a portion adjacent to the radial center of the shielding plate 142 from the light source 191 may hardly be emitted out of the support modules 140, 150.

Based on this, the passage hole 149 may be formed at the radial center of the shielding plate 142, which is not closely related to emission of light, for example. Light may not be reflected properly at the portion at which the passage hole 149 is formed. However, when the passage hole 149 is formed at a portion which is not closely related to emission of light even if light is reflected in the portion, the passage hole 149 has no significant effect on an increase or decrease in the amount of light emission.

For example, the electric wire H may be provided in the form of a harness provided with a terminal. To connect the electric wire H and the board 193, the board 193 may be provided with a connector 197. The connector 197 together with the light source 191 may be disposed on a lower surface of the board 193. That is, the connector 197 may be disposed on a same flat surface as the light source 191.

The connector 197 may be disposed at a position closer to the center of the oval forming the shielding plate 142 than to the focal point of the oval. For example, the connector 197 may be disposed in an inner area surrounded by the plurality of light sources 191.

The position may be a position which is not closely related to a path in which the light source 191 irradiates light and a path in which the reflector 195 reflects light, and is close to the passage hole 149. Accordingly, the electric wire H may be prevented from interfering with a path of light and be shortened.

Figure 15:
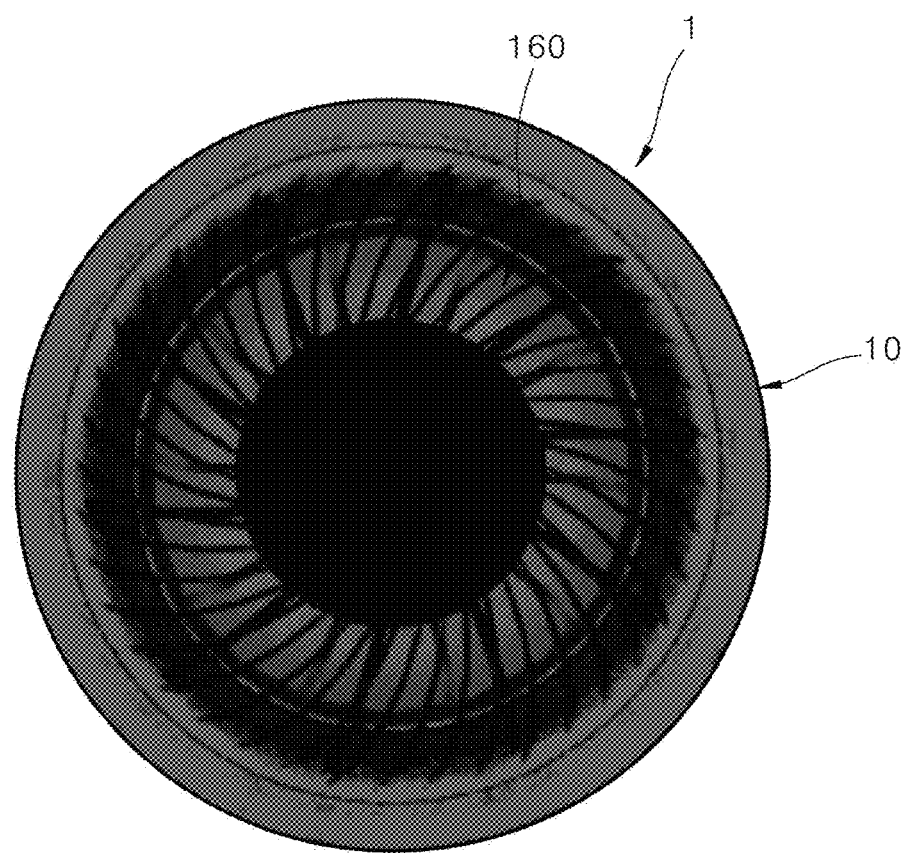
FIG. 15 is a view showing a state, in which lighting of the portable air purifier according to an embodiment is implemented, as seen from above.

FIG. 15 is a view showing a state, in which lighting of the portable air purifier according to an embodiment is implemented, as seen from above. As illustrated in FIGS. 2 to 4, 13 and 14, the portable air purifier 1 according to this embodiment may be provided with the lighting portion 190, and provide a lighting function through the lighting portion 190. The lighting portion 190 may include the light source 191 and the reflector 195, and light irradiated from the light source 191 downward may be reflected upward by the reflector 195 and emitted out of the support modules 140, 150.

The light source 191 may be disposed near the edge of the support modules 140, 150, and light irradiated from the light source 191 may be reflected upward by the reflector 195 mostly to the gap formed at the edge of the support modules 140, 150. The light irradiated from the light source 191 may be reflected upward by the reflector 195 having an oval shape, and spread uniformly to the gap formed at the edge of the support modules 140, 150. The light emitted out of the support modules 140, 150 may be emitted from the upper portion of the portable air purifier 1 through the second discharge opening 160a of the discharge outlet 160 or through the gap between the discharge outlet 160 and the second case 30.

For example, the light emitted from the upper portion of the portable air purifier 1 may be displayed as a concentric circle which is a combination of a ring shape corresponding to the shape of the second discharge opening 160a of the discharge outlet 160, and a ring shape corresponding to the shape of the gap between the discharge outlet 160 and the second case 30. Light reflected by the reflector 195 having an oval shape may spread uniformly to the gap formed at the edge of the support modules 140, 150, and the light having spread uniformly may be displayed as a concentric circle, to implement lighting. That is, the reflector 195 having an oval shape may help to improve light uniformity when lighting is implemented. In this case, the implemented lighting may be provided as indirect lighting that leaks through a gap at a front surface of the portable air purifier 1.

The light source 191 may include an LED than can implement a variety of color temperatures and colors. Lighting implemented by the lighting portion 190 provided with the light source 191 may be implemented depending on a user's taste or in a way which a state of surrounding air or an operation state of the portable air purifier 1 is reflected.

For example, a color temperature or a color of lighting implemented by the lighting portion 190 may be selected based on a user's manipulation. As another example, a color temperature or a color of lighting implemented by the lighting portion 190 may vary depending on a state of surrounding air and an operation speed of the fan module 70.

In this embodiment, a structure in relation to the lighting portion 190 may be disposed in a space formed between the fan cover 140 for guiding discharge of purified air, and the holder body 151 that supports the discharge outlet 160.

The portable air purifier 1 provided with the lighting portion 190 described above may implement a lighting function effectively without increasing its entire size. Additionally, assembly work for mounting the lighting portion 190 may be completed simply by fitting the board 193 in which the light source 191 is mounted onto the fan cover 140 and by coupling the fan cover 140 and the holder body 151. Further, structure such as the first mount 153 and the second mount 145 for coupling the fan cover 140 and the holder body 151 may help to improve rigidity of the fan cover 140 and rigidity of the holder body 151. Thus, provided is a portable air purifier 1 that can provide a lighting function, ensure ease of assembly and have improved rigidity.

Embodiments disclosed herein provide a portable air purifier that can implement lighting capable of visualizing and displaying information on air quality, for example, effectively. Further, embodiments disclosed herein improve light uniformity at a time of implementation of lighting.

Embodiments disclosed herein apply a lighting function to a portable air purifier without increasing the entire size of the device. Embodiments disclosed herein also arrange a cable needed to implement lighting in such a way that the cable does not interfere with air flow.

Additionally, embodiments disclosed herein improve rigidity of a structure in relation to implementation of a lighting function without increasing the entire size of the device. Embodiments disclosed herein further provide a portable air purifier that implements a lighting function, ensures ease of assembly and has improved rigidity.

In a portable air purifier according to embodiments disclosed herein, a fan module is disposed between a suction opening and a discharge opening, a filter is disposed between the suction opening and the fan module, and a lighting portion is disposed between the discharge opening and the fan module. A fan cover is disposed between a discharge opening and a fan module, a holder configured to support a discharge outlet provided with the discharge opening is disposed between the fan cover and the discharge opening, and a lighting portion is disposed between the fan cover and the holder.

A plurality of light sources may be mounted onto a board of the lighting portion. Each of the light sources may irradiate light to a reflector below the light sources.

The board may be disposed between the reflector below the board and the truncated cone-shaped holder over the board. The reflector may include a curved surface, such that light reflected by the reflector is mostly reflected toward an edge of the reflector. The reflector may have an oval shape, for example. Accordingly, light irradiated from the light source may spread evenly through the oval-shaped reflector, thereby improving light uniformity at a time of implementation of lighting.

Additionally, an upper surface of a shielding plate disposed at a center of the fan cover may form the reflector. Further, a passage hole may be disposed in an approximately central portion of the reflector, and formed in a way that the passage hole passes through the shielding plate in an vertical direction. An electric wire connected to the board may be withdrawn from a lower portion of the shielding plate through the passage hole, and extend to an inner circumferential surface of a housing between the fan module and the shielding plate in a lateral direction.

A portable air purifier according to embodiments disclosed herein may include a housing provided with a suction opening; a discharge outlet provided with a discharge opening disposed above the suction opening; a fan module disposed between the suction opening and the discharge opening; a support module disposed between the fan module and the discharge outlet and configured to support the discharge outlet; and a lighting portion installed in the support module and configured to irradiate light rays, and a gap between the discharge outlet and the housing, or the discharge opening may form a passage for emitting at least a portion of the light rays irradiated from the lighting portion out of the discharge outlet or the housing. At least a portion of the light rays irradiated from the lighting portion may be emitted out of the discharge outlet through the discharge opening or emitted out of the housing through the gap between the discharge outlet and the housing.

The fan module may be disposed in the housing, and disposed between the suction opening and the discharge opening. The fan module may create an air flow in which air is suctioned into the housing through the suction opening and discharged out of the discharge outlet through the discharge opening.

The support module may include a fan cover disposed between the fan module and the discharge outlet, and a support disposed between the fan cover and the discharge opening and configured to support the discharge outlet. The lighting portion may be disposed in a space surrounded by the fan cover and the support.

The lighting portion may include a light source configured to irradiate light rays toward a lower portion of the support, and a reflector disposed below the light source and configured to reflect light rays irradiate from the light source toward the discharge opening. The reflector may have a shape including a curved surface which is concave downward.

The reflector may have a shape including at least a portion of an oval and be formed in a way that a horizontal center is disposed in a lowermost portion. The light source may be disposed closer to a focal point of an oval including the reflector than to a center of the oval.

The fan cover may include a shielding plate disposed between the discharge opening and the fan module, and a plurality of guide vanes respectively that extend from the shielding plate in a centrifugal direction and spaced a predetermined distance apart from one another along a circumferential direction of the shielding plate. The light source may be disposed over the shielding plate, and the reflector may be disposed at the shielding plate.

The reflector may include one lateral surface of the shielding plate, which faces the light source.

The support may include a holder disposed between the shielding plate and the discharge outlet and coupled to the shielding plate, and a support rod coupled to the holder and configured to support the discharge outlet in a posture changeable manner. The light source may be disposed in a space surrounded by the shielding plate and the holder.

The shielding plate and the holder may be disposed in an vertical direction, a lower end edge of the holder, facing the shielding plate, may be disposed inside of the shielding plate in a lateral direction thereof, and a ring-shaped gap may be formed between an upper end edge of the shielding plate and the lower end edge of the holder. The upper end edge of the shielding plate and the lower end edge of the holder may be respectively formed into a circle taking a same axis as a center, and a radius of the upper end edge of the shielding plate may be greater than a radius of the lower end edge of the holder.

The portable air purifier according to embodiments disclosed herein may further include a first mount that protrudes from the lower end edge of the holder in the centrifugal direction, and a second mount disposed at the shielding plate and coupled to the first mount. The second mount may include an outer projection disposed near an edge of the shielding plate and coupled to the first mount in the vertical direction, and an inner projection disposed further inward than the outer projection in a lateral direction of the shielding plate and configured to support the first mount inside of the shielding plate in the lateral direction thereof.

The lighting portion may further include a board onto which the light source is mounted. The board may be fixed between the shielding plate and the holder, over the light source. The holder may have a shape including a solid figure in which a bottom surface forming a lower end edge of the holder is formed into a circle, and a lateral surface forming a lateral wall of the holder may be formed into a curved surface that is gradually narrowed upward. The board may be mounted onto the inner projection, the lower end edge of the holder may limit a lateral movement of the board while surrounding the board outside the board in a lateral direction thereof, and the lateral wall of the holder may limit an upward movement of the board, over the board.

The shielding plate may be provided with a passage hole formed to pass through the shielding plate. An electric wire may pass through the shielding plate through the passage hole. The passage hole may be disposed closer to a center of an oval including the shielding plate than a focal point of the oval.

A connector may be disposed on the board. The connector may connect to the electric wire to electrically connect the board and the electric wire. The connector may be disposed closer to the center of the oval including the shielding plate than to the focal point of the oval.

In a portable air purifier according to embodiments disclosed herein, light irradiated from a light source may come out of the portable air purifier through an edge of a discharge, thereby making it possible to effectively apply a lighting function to the portable air purifier. Light irradiated from the light source may spread evenly through a reflector having an oval shape, thereby making it possible to improve light uniformity at a time of implementation of lighting. Structure in relation to implementation of a lighting function may be disposed in a space formed between a fan cover that guides discharge of purified air and a holder that supports a discharge outlet, thereby making it possible to effectively applying the lighting function to the portable air purifier without increasing the entire size of the device.

In the portable air purifier, while rigidity of the holder and the fan cover may improve as a result of coupling between a first mount disposed at a lower end of the holder and a second mount disposed at the reflector, the rigidity of the holder itself may be improved using a structure like the first mount, and the rigidity of the fan cover itself may be improved using a structure like the second mount. That is, in the portable air purifier, the rigidity of the holder and the fan cove themselves may be improved using a structure provided for coupling between the holder and the fan cover, and the holder and the fan cover may be coupled and their rigidity may be improved as a result of the coupling between the first mount and the second mount, thereby making it possible to improve rigidity of a structure in relation to implementation of a lighting function without increasing the entire size of the device.

Further, in the portable air purifier, assembly for implementing visible lighting may be performed only by fitting a board into the fan cover and coupling the fan cover and the holder, thereby making it possible to provide a portable air purifier that may provide a lighting function, ensure easy of assembly, and have improved rigidity.

Embodiments are described above with reference to a number of illustrative embodiments thereof. However, the embodiments are not intended to be limited to the embodiments and drawings set forth herein, and numerous other modifications and embodiments may be devised by one skilled in the art without departing from the technical spirit. The technical protection scope should be defined according to the appended claims.

It will be understood that when an element or layer is referred to as being "on" another element or layer, the element or layer can be directly on another element or layer or intervening elements or layers. In contrast, when an element is referred to as being "directly on" another element or layer, there are no intervening elements or layers present. As used herein, the term "and/or" includes any and all combinations of one or more of the associated listed items.

It will be understood that, although the terms first, second, third, etc., may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section could be termed a second element, component, region, layer or section without departing from the teachings of the present invention.

Spatially relative terms, such as "lower", "upper" and the like, may be used herein for ease of description to describe the relationship of one element or feature to another element (s) or feature(s) as illustrated in the figures. It will be understood that the spatially relative terms are intended to encompass different orientations of the device in use or operation, in addition to the orientation depicted in the figures. For example, if the device in the figures is turned over, elements described as "lower" relative to other elements or features would then be oriented "upper" relative to the other elements or features. Thus, the exemplary term "lower" can encompass both an orientation of above and below. The device may be otherwise oriented (rotated 90 degrees or at other orientations) and the spatially relative descriptors used herein interpreted accordingly.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Embodiments are described herein with reference to cross-section illustrations that are schematic illustrations of idealized embodiments (and intermediate structures). As such, variations from the shapes of the illustrations as a result, for example, of manufacturing techniques and/or tolerances, are to be expected. Thus, embodiments should not be construed as limited to the particular shapes of regions illustrated herein but are to include deviations in shapes that result, for example, from manufacturing.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Any reference in this specification to "one embodiment," "an embodiment," "example embodiment," etc., means that a particular feature, structure, or characteristic described in connection with the embodiment is included in at least one embodiment. The appearances of such phrases in various places in the specification are not necessarily all referring to the same embodiment. Further, when a particular feature, structure, or characteristic is described in connection with any embodiment, it is submitted that it is within the purview of one skilled in the art to effect such feature, structure, or characteristic in connection with other ones of the embodiments.

Although embodiments have been described with reference to a number of illustrative embodiments thereof, it should be understood that numerous other modifications and embodiments can be devised by those skilled in the art that will fall within the spirit and scope of the principles of this disclosure. More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. A portable air purifier, comprising:
   a housing including a suction opening;
   a discharge outlet including a discharge opening disposed above the suction opening;
   a fan module disposed between the suction opening and the discharge outlet;
   a support module disposed between the fan module and the discharge outlet and configured to support the discharge outlet; and
   a lighting portion installed in the support module and configured to irradiate light rays, wherein a gap between the discharge outlet and the housing, or the discharge opening forms a passage for emitting at least a portion of the light rays irradiated from the lighting portion out of the discharge outlet or the housing, wherein the support module comprises:
- a fan cover disposed between the fan module and the discharge outlet; and
- a support disposed between the fan cover and the discharge opening and configured to support the discharge outlet, wherein the lighting portion is disposed in a space surrounded by the fan cover and the support, and wherein the lighting portion comprises:
  - a light source configured to irradiate light rays toward a lower portion of the support; and
  - a reflector disposed below the light source and configured to reflect light rays irradiate from the light source toward the discharge opening.

2. The portable air purifier of claim 1, wherein the reflector has a shape comprising a curved surface which is concave downward.

3. The portable air purifier of claim 2, wherein the reflector has a shape comprising at least a portion of an oval and is formed in a way such that a lateral center thereof is disposed at a lowermost portion.

4. The portable air purifier of claim 3, wherein the light source is disposed closer to a focal point of the oval comprising the reflector than to a center of the oval.

5. The portable air purifier of claim 1, wherein the fan cover, comprises:
- a shielding plate disposed between the discharge opening and the fan module; and
- a plurality of guide vanes that respectively extends from the shielding plate in a centrifugal direction and spaced a predetermined distance apart from one another along a circumferential direction of the shielding plate, wherein the light source is disposed over the shielding plate, and the reflector is disposed at the shielding plate.

6. The portable air purifier of claim 5, wherein the reflector comprises one lateral surface of the shielding plate, the one lateral surface facing the light source.

7. The portable air purifier of claim 5, wherein the support comprises:
- a holder body disposed between the shielding plate and the discharge outlet and coupled to the shielding plate; and
- a support rod coupled to the holder and configured to support the discharge outlet in a posture changeable manner, wherein the light source is disposed in a space surrounded by the shielding plate and the holder body.

8. The portable air purifier of claim 7, wherein the shielding plate and the holder body are disposed in a vertical direction, wherein a lower end edge of the holder body, facing the shielding plate, is disposed inside of the shielding plate in a lateral direction thereof, and wherein a ring-shaped gap is formed between an upper end edge of the shielding plate and the lower end edge of the holder body.

9. The portable air purifier of claim 8, wherein the upper end edge of the shielding plate and the lower end edge of the holder body are respectively formed into a circle taking a same axis as a center, and a radius of the upper end edge of the shielding plate is greater than a radius of the lower end edge of the holder body.

10. The portable air purifier of claim 7, further comprising:
- a first mount that protrudes from the lower end edge of the holder body in the centrifugal direction; and
- a second mount disposed at the shielding plate and coupled to the first mount.

11. The portable air purifier of claim 10, wherein the second mount, comprises:
- an outer projection disposed near an edge of the shielding plate and coupled to the first mount in the vertical direction; and
- an inner projection disposed further inward than the outer projection in a lateral direction of the shielding plate and configured to support the first mount inside of the shielding plate in the lateral direction thereof.

12. The portable air purifier of claim 11, wherein the lighting portion further comprises a board onto which the light source is mounted, and wherein the board is fixed between the shielding plate and the holder body, over the light source.

13. The portable air purifier of claim 12, wherein the holder body has a shape comprising a solid figure in which a bottom surface forming a lower end edge of the holder body is formed into a circle, and a lateral surface forming a lateral wall of the holder body is formed into a curved surface that is gradually upwardly narrowed, wherein the board is mounted onto the inner projection, the lower end edge of the holder limits a lateral movement of the board while surrounding the board outside the board in a lateral direction thereof, and wherein the lateral wall of the holder limits an upward movement of the board, on the board.

14. The portable air purifier of claim 5, wherein the portable air purifier further comprises a board onto which the light source is mounted, and an electric wire that connects to the board, wherein the shielding plate is provided with a passage hole, and wherein the electric wire passes through the passage hole in the shielding plate.

15. The portable air purifier of claim 14, wherein the shielding plate has a shape comprising at least a portion of an oval, and a lateral center of the shielding plate is disposed at a lowermost portion, wherein the light source is disposed closer to a focal point of the oval comprising the shielding plate than a center of the oval, and wherein the passage hole is disposed closer to the center of the oval comprising the shielding plate than the focal point of the oval.

16. The portable air purifier of claim 15, wherein a connector is disposed on the board, and the connector connects to the electric wire to electrically connect the board and the electric wire, and wherein the connector is disposed closer to the center of the oval comprising the shielding plate than to the focal point of the oval.

17. A portable air purifier, comprising:
- a housing including a suction opening;
- a discharge outlet including a discharge opening disposed above the suction opening;
- a fan module disposed between the suction opening and the discharge outlet;
- a support module disposed between the fan module and the discharge outlet and configured to support the discharge outlet; and
- a lighting portion installed in the support module and including at least one light source configured to irradiate light rays and a reflector disposed below the at least one light source and configured to reflect light rays irradiate from the at least one light source toward the discharge opening, wherein a gap between the discharge outlet and the housing, or the discharge opening forms a passage for emitting at least a portion of the light rays irradiated from the at least one light source out of the discharge outlet or the housing.

* * * * *